(12) United States Patent
Dalal et al.

(10) Patent No.: US 8,323,258 B2
(45) Date of Patent: Dec. 4, 2012

(54) QUIET ADHESIVE FASTENING SYSTEM FOR A DISPOSABLE ABSORBENT ARTICLE

(75) Inventors: Urmish Popatlal Dalal, Milford, OH (US); Mark William Hamersky, Indian Springs, OH (US); Kathleen Marie Lawson, West Chester, OH (US); George Christopher Dobrin, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 515 days.

(21) Appl. No.: 11/881,515

(22) Filed: Jul. 27, 2007

(65) Prior Publication Data

US 2009/0030395 A1 Jan. 29, 2009

(51) Int. Cl.
*A61F 13/15* (2006.01)
(52) U.S. Cl. .............. 604/389; 604/367; 604/385.03
(58) Field of Classification Search .......... 604/385.03, 604/386–394, 367
See application file for complete search history.

(56) References Cited

U.S. PATENT DOCUMENTS

| | | | |
|---|---|---|---|
| 3,848,594 A | 11/1974 | Buell | |
| 3,860,003 A | 1/1975 | Buell | |
| 4,662,875 A | 5/1987 | Hirotsu et al. | |
| 4,699,622 A | 10/1987 | Toussant et al. | |
| 4,846,815 A | 7/1989 | Scripps | |
| 4,894,060 A | 1/1990 | Nestegard | |
| 4,940,464 A | 7/1990 | Van Gompel et al. | |
| 4,946,527 A | 8/1990 | Battrell | |
| 4,963,140 A | 10/1990 | Robertson et al. | |
| 5,092,861 A | 3/1992 | Nomura et al. | |
| 5,110,882 A | 5/1992 | Hamada et al. | |
| 5,151,092 A | 9/1992 | Buell et al. | |
| 5,221,274 A | 6/1993 | Buell et al. | |
| 5,242,436 A | 9/1993 | Weil et al. | |
| 5,246,433 A | 9/1993 | Hasse et al. | |
| 5,499,978 A | 3/1996 | Buell et al. | |
| 5,507,736 A | 4/1996 | Clear et al. | |
| 5,554,145 A | 9/1996 | Roe et al. | |
| 5,569,234 A | 10/1996 | Buell et al. | |
| 5,580,411 A | 12/1996 | Nease et al. | |
| 5,591,152 A | 1/1997 | Buell et al. | |
| 5,776,614 A | 7/1998 | Cifuentes et al. | |
| 5,897,545 A | 4/1999 | Kline et al. | |
| 5,957,908 A | 9/1999 | Kline et al. | |
| 6,004,306 A | 12/1999 | Robles et al. | |
| 6,007,527 A | 12/1999 | Kawaguchi et al. | |
| 6,096,420 A * | 8/2000 | Wilhoit et al. | 428/343 |
| 6,120,487 A | 9/2000 | Ashton | |
| 6,120,489 A | 9/2000 | Johnson et al. | |
| 6,432,098 B1 | 8/2002 | Kline et al. | |

(Continued)

OTHER PUBLICATIONS

International Search Report, data Feb. 2, 2009, 4 pages.

*Primary Examiner* — Michele M Kidwell
(74) *Attorney, Agent, or Firm* — Kathleen Y. Carter; John G. Powell

(57) ABSTRACT

A quiet fastening system that includes a silicone-based adhesive. The silicone-based adhesive is applied to an engaging member or receiving member of the fastening system. The engaging member and receiving member are releasably joined to engage the quiet fastening system. When disengaged, the quiet fastening system exhibits a noise level of less than 15 dB. The quiet fastening system also exhibits desirable Shear Hang Time and Peel Force.

15 Claims, 10 Drawing Sheets

U.S. PATENT DOCUMENTS

| | | |
|---|---|---|
| 6,511,466 B1 | 1/2003 | Nagami et al. |
| 6,706,390 B1 | 3/2004 | Schmitz et al. |
| 2002/0013386 A1 | 1/2002 | Aoki |
| 2003/0233082 A1 | 12/2003 | Kline et al. |
| 2005/0136266 A1 | 6/2005 | Zhou et al. |
| 2006/0008662 A1 | 1/2006 | Arai et al. |

* cited by examiner

QUIET ADHESIVE FASTENING SYSTEM FOR A DISPOSABLE ABSORBENT ARTICLE

FIELD OF THE INVENTION

The invention is related to a quiet adhesive fastening system for use with disposable absorbent articles. Specifically, certain embodiments are directed to disposable diapers with a refastenable fastening system that includes a quiet, silicone-based adhesive.

BACKGROUND OF THE INVENTION

Fastening systems are widely used in a variety of applications where closure of components is required. Certain fastening systems are refastenable, that is, they are capable of multiple openings and closures. Items such as diapers and containers storing foodstuff or other consumer goods are commonly equipped with a fastening system that may be refastened. Such refastenable fastening systems may include one of a variety of mechanical fastening systems or adhesive fastening systems. While mechanical and adhesive fastening systems provide certain consumer benefits, each system also includes features that many consumers of absorbent articles find undesirable.

Mechanical fastening systems include hook and loop fasteners and variants such as mushroom-shaped fasteners. These types of mechanical fasteners may have a tendency to attach to undesired surfaces such as clothing, carpet, or the wearer. Furthermore, hooks are generally rigid and may be a source of irritation if used in products which are placed in close contact to a wearer's skin. Another problem often associated with mechanical type fasteners is that they may become damaged during the high-speed formation process required for commercially viable manufacture of consumer goods such as diapers. For example, hooks tend to get damaged during manufacture, and other mechanical type fasteners such as buttons, tab and slots, or the like can also become damaged, torn, or otherwise impacted by high speed handling. Still another problem is that mechanical fasteners may generate undesirable noise when disengaged. However, attempts to reduce the amount of noise often associated with mechanical fasteners may result in an undesirable change in the performance characteristics of the fastener, for example, reduced fastening strength.

Like mechanical fastening systems, adhesive fastening systems also have drawbacks. One example of such a drawback is the noise produced when the fastening system is disengaged. Adhesive fastening systems are commonly used with disposable absorbent articles, for example, diapers worn by babies, in order to join the front and back waist regions together. In the example of a baby wearing a diaper, there may be instances when a caregiver of the baby desires to unfasten the diaper in order to check if the diaper has been soiled by urine or feces. Upon discovering any such soiling, the caregiver will typically replace the soiled diaper with a clean diaper. Some diaper wearers, for example, newborn babies, may soil several diapers a day, including during the time the wearer is sleeping. In such instances, a caregiver of the wearer may wish to check and/or change the wearer's diaper while the wearer is asleep. However, due to the noise generated when the fastening system is disengaged or the sensitivity of the wearer to noise, a caregiver may be reluctant to change the wearer's diaper while the wearer is asleep for fear of waking the wearer. This reluctance may translate into prolonged exposure of the skin of the wearer to bodily exudates. Increased exposure of skin to bodily exudates such as fecal matter is typically undesirable since it is commonly known that such exposure can lead to increased skin irritation and other ailments.

In addition to disposable absorbent articles, other articles of commerce may also benefit from the use of quiet fasteners. For example, some people may find the noise produced by unfastening a particular type of fastener, such as a hook and loop type mechanical fastener, to be undesirable. Still others may find themselves in an environment, such as a work environment, where the noise produced by unfastening a typical fastener may be unacceptably distracting to coworkers.

Accordingly, it would be desirable to provide a quiet fastening system. It would also be desirable to provide a disposable absorbent article with a quiet fastening system.

SUMMARY OF THE INVENTION

In order to provide a solution to the problems set forth above, at least one embodiment provides for a quiet adhesive fastening system. The quiet adhesive fastening system includes one or more engaging members that each includes an engaging surface. The quiet adhesive fastening system also includes one or more receiving member that each includes a receiving surface. The quiet adhesive fastening system further includes a silicone-based adhesive disposed on at least one engaging member. At least one receiving member is configured to receive at least one engaging member. When the engaging surface of the engaging member is brought into contact with the receiving surface of the receiving member, the silicon-based adhesive releasably joins the engaging member and the receiving member together with an adhesive bond. The quiet fastening system exhibits a peel noise value of less than 25 dB according to the Peel Noise test when the fastening system is disengaged.

DETAILED DESCRIPTION OF THE INVENTION

Figure 1:
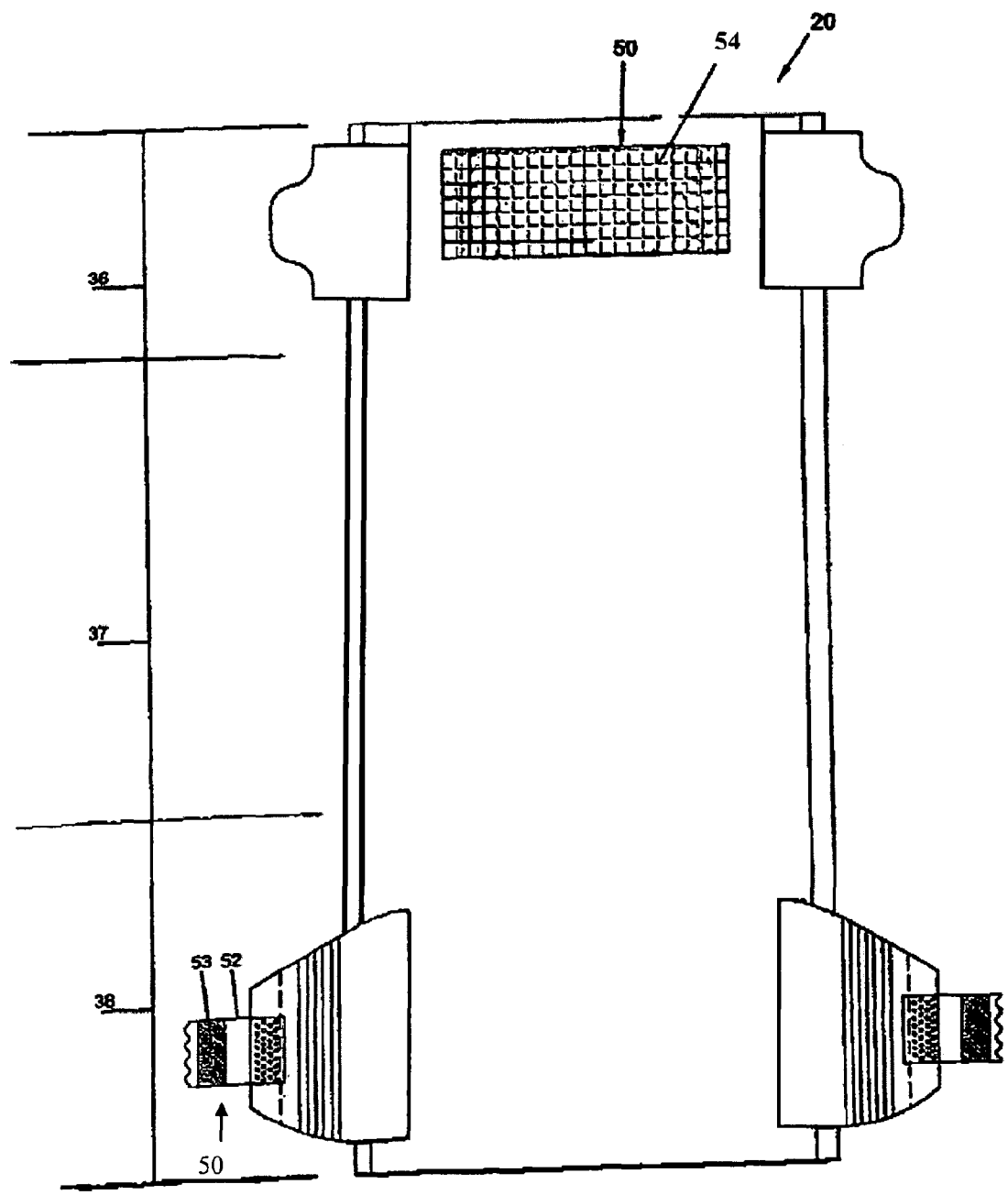
FIG. 1 is a plan view of a disposable absorbent article in a flat, uncontracted state.

As used herein, the term "disposed" is used to mean that an element(s) is formed (joined and positioned) in a particular place or position as a unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

As used herein the term "refastenable" refers to the attachment of two or more elements or portions of elements together in a manner such that they can be separated and re-attached without substantial degradation of fastener performance or damage to surrounding components of the article that would impair the article's continued use. It will be appreciated that a refastenable component need not have an infinite life span, but it is sufficient that the components attached in a refastenable manner can be separated and re-attached successively several times over the typical use life span of the article. It will also be appreciated that the aggressiveness of actual fastening may be reduced significantly from fastening to refastening in absolute terms, but that such reduction is not "substantial degradation" of fastener performance if the resulting refastened strength is sufficient for the fastening system's purpose of use.

As used herein, the term "refastening event" refers to the disengagement and reengagement of a refastenable fastening system.

As used herein, "adherent" refers to a composition or material, such as, for example, a silicone-based adhesive, which demonstrates adhesion when applied to another material. An adherent may connect to a variety of adherends indiscriminately or may connect only to a particular adherend.

As used herein, "adherend" refers to a material or substrate, such as, for example, a polyethylene receiving member, which connects to an adherent.

As used herein, the terms "typical adhesive" and "traditional adhesive" are interchangeable and generally refer to an adherent which demonstrates adhesion when applied to an adherend generally (e.g. material is not specially selected). Traditional adhesive materials generally connect to other adherends indiscriminately and may stick to a variety of adherends. Traditional adhesives are often tacky and noisy. Nonlimiting examples of traditional adhesives include rubber-based pressure sensitive adhesives and acrylic pressure sensitive adhesives.

As used herein, "traditional adhesive fastening system" refers to a fastening system that relies on at least one traditional adhesive to operatively join one component of the fastening system to itself or another component.

As used herein, "silicone-based adhesive" means an adhesive comprising at least one silicone polymer. The silicone polymer can be formed by any crosslinking mechanism commonly known in the art, such as, for example, hydrosilation or silanol condensation and may be delivered from solvent or as an emulsion from water/oil. Silicone polymers suitable for use with certain embodiments may include filler particles, such as, for example, silica particles, MQ silicone resins, and $TiO_2$. The silicone polymers for use with certain embodiments may also include tackifier resins to increase the glass transition temperature of the polymer. Silicone-based adhesives typically adhere to non-tacky adherends and adherend surfaces. Particularly suitable silicone-based adhesives are pressure sensitive adhesives. Examples of silicone-based adhesives and silicone-based pressure sensitive adhesives can be found in U.S. Pat. No. 5,110,882 to Hamada, et al.; U.S. Pat. No. 5,776,614 to Cifuentes, et al.; and U.S. Pat. No. 6,706,390 to Schmitz, et al., and U.S. Publication Nos. 20050136266, to Zhou, et al.; 20060008662 to Arai, et al.; and 20020013386 to Aoki, et al.

As used herein, "silicone adhesive fastening system" refers to a fastening system that relies on at least one silicone-based adhesive to operatively join one component of the fastening system to itself or another component.

As used herein "quiet adhesive fastening system" generally refers to a fastening system comprising a silicone-based adhesive that, when disengaged, exhibits a noise level of less than 25 dB as measured according to the Peel Noise Test.

As used herein, "accelerated aging process" refers to an engaged fastening system being subjected to a temperature of 60° C. and an evenly distributed, continuous pressure of 0.8 $N/cm^2$ for 3 days. An "aged" sample is a sample that has been subjected to the accelerated aging process. A "fresh" sample is a sample that has not been subjected to the accelerated aging process, and typically is a sample that is tested within 10 minutes of its construction, but need not necessarily be so. Commercially available pre-engaged fastening systems that have been incorporated into an article are presumed to be aged.

As used herein the term "pre-engaged" refers to a fastening system that is manufactured so that elements of the fastening system are engaged, affixed, or otherwise joined together.

Traditional fastening systems used in connection with various articles of commerce, such as, for example, disposable absorbent articles, may employ a variety of commonly known fasteners. A fastening system may include permanent fasteners, refastenable fasteners, or some combination of the two. It is commonly known that traditional refastenable fasteners may produce an undesirable noise or an undesirable amount of noise when the fastener is disengaged. This noise may be more than 25 dB over the background noise level. Especially problematic is when the traditional fastening system is unfastened in the presence of someone who may be disturbed by loud noise, such as, for example, a sleeping baby.

Surprisingly, it has been found that by including a silicone-based adhesive in a fastening system, such as, for example, a silicone-based pressure sensitive adhesive, the noise produced by disengaging a refastenable fastener may be reduced or even eliminated. When used in conjunction with the fastening system of a disposable absorbent article, such as, for example, a diaper, the noise produced during a refastening event may be reduced to a tolerable, desirable or even undetectable level. With such reduction in noise level, the likelihood of producing a noise that disturbs others may be reduced or even eliminated.

FIG. 1 is a plan view of an exemplary, non-limiting embodiment of a diaper 20 in a flat, uncontracted state. The diaper 20 shown in FIG. 1 has a front waist region 36, a rear waist region 38 opposed to the front waist region 36, and a crotch region 37 located between the front waist region 36 and the rear waist region 38. The waist regions 36 and 38 generally comprise those portions of the diaper 20 which, when worn, encircle the waist of the wearer. The waist regions 36 and 38 may include elastic elements that gather the material in the front and/or back waist region 36, 38 about the waist of the wearer to provide improved fit and containment. The crotch region 37 is that portion of the diaper 20 which, when the diaper 20 is worn, is generally positioned between the legs of the wearer. Nonlimiting examples of suitable diaper configurations are described generally in U.S. Pat. Nos. 3,860,003; 5,151,092; 5,221,274; 5,554,145; 5,569,234; 5,580,411; and 6,004,306.

The diaper 20 may include a fastening system 50, such as, for example, a refastenable fastening system. When fastened, the fastening system 50 typically interconnects the front waist region 36 and the rear waist region 38 resulting in a waist circumference that generally encircles a wearer of the diaper 20. Examples of fastening systems are disclosed in U.S. Pat. Nos. 3,848,594; 4,662,875; 4,846,815; 4,894,060; 4,946,527; 5,151,092; 5,221,274; and 6,432,098. The fastening system 50 may also provide a means for holding the article in a disposal configuration as disclosed in U.S. Pat. No. 4,963, 140. The fastening system 50 may include primary and secondary fastening systems, as disclosed in U.S. Pat. No. 4,699, 622. The fastening system 50 may be constructed to reduce shifting of overlapped portions or to improve fit as disclosed in U.S. Pat. Nos. 5,242,436; 5,499,978; 5,507,736; and 5,591, 152.

FIG. 1 shows a fastening system 50 having an engaging member 52 and a receiving member 54. The receiving member 54 may be configured to receive the engaging member 52 such that the engaging member 52 and the receiving member 54, when engaged, cooperatively form a waist circumference. The engaging member 52 may comprise an engaging surface 53 that enables a user to engage the fastening system 50, for example, by contacting the engaging surface 53 to the receiving member 54 and thereby affixing the engaging member 52 to the receiving member 54. The fastening system 50 shown in FIG. 1 may include an engaging member 52 comprising an adherent and a receiving member 54 comprising an adherend. The adherent may include, for example, one or more silicone-based adhesives disposed on the engaging surface 53. The adherend may include a polymer film or nonwoven web. Suitable polymers for use with certain embodiments include without limitation polyolefins, styrenic block copolymers and other suitable polymer and polymer combinations commonly known in the art. The adherent and adherend may cooperatively provide an adhesive bond capable of joining the engaging member 52 to the receiving member 54. While FIG. 1 depicts the engaging surface 53 as encompassing only a particular portion of the engaging member 52, it is to be understood that the engaging surface 53 may encompass any portion of the engaging member 52.

In certain embodiments the fastening system 50 may be configured such that the engaging members 52 can be overlapped. A portion of an engaging member 52, for example, a portion not having a silicone-based adhesive disposed thereon, may be configured to be a receiving surface. In such embodiments, it may be advantageous to provide a receiving surface on the backside of the engaging member (i.e., the surface of the engaging member opposite the surface having the adhesive disposed thereon) in order to provide a suitable receiving surface in situations where the engaging members are in an overlapped configuration.

In certain embodiments, the engaging member 52 may include a silicone-based adhesive and a traditional adhesive. In such embodiments, the engaging member 52 may be configured as a laminate structure such that a film or other suitable substrate comprising the silicone-based adhesive is joined to the engaging member by way of the traditional adhesive. The engaging member for such a fastening system may be provided as roll stock prior to being incorporated into the fastening system. When an engaging member according to certain embodiments comprises a silicone-based adhesive as well as a traditional adhesive and is provided as roll stock, it may be desirable to use a release coating or release paper, for example, a silicone release coating, in order to reduce the force required to unwind the roll stock and/or the unwind noise produced during a manufacturing process.

In certain embodiments of the invention, the fastening system may comprise an integral part of another absorbent article component. That is, an article may include a fastening system constructed as all or part of another article component. For example, a diaper may include a fastening system that comprises all or part of any one of the backsheet, topsheet, ear, or waistpanel. Suitable example of integral fasteners can be found in copending U.S. Publication No. 20070143972, filed by Kline, et al., on Dec. 14, 2006 and copending U.S. application Ser. No. 11/638,748, filed by Kline, et al, on Dec. 14, 2006.

Figure 2A:
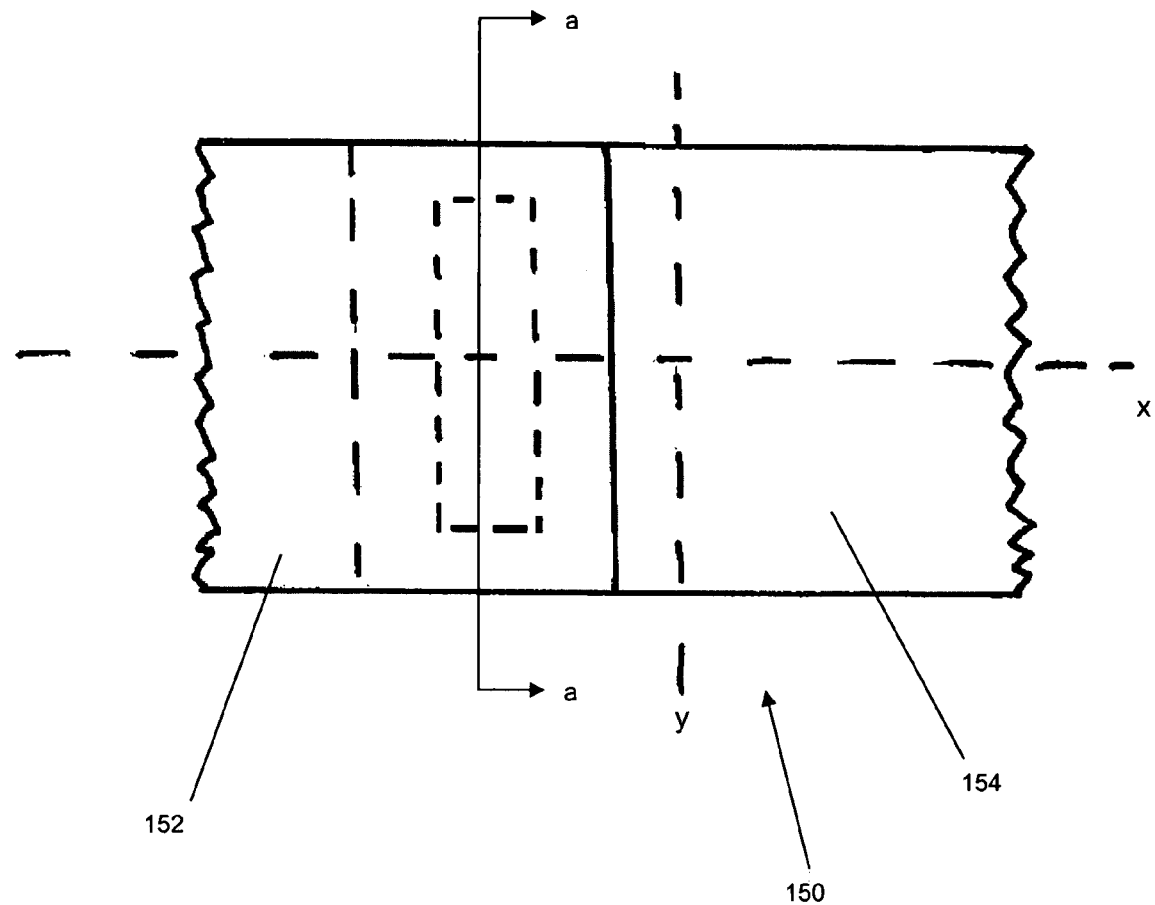
FIG. 2A is a plan view of an example of a fastener.
Figure 2B:
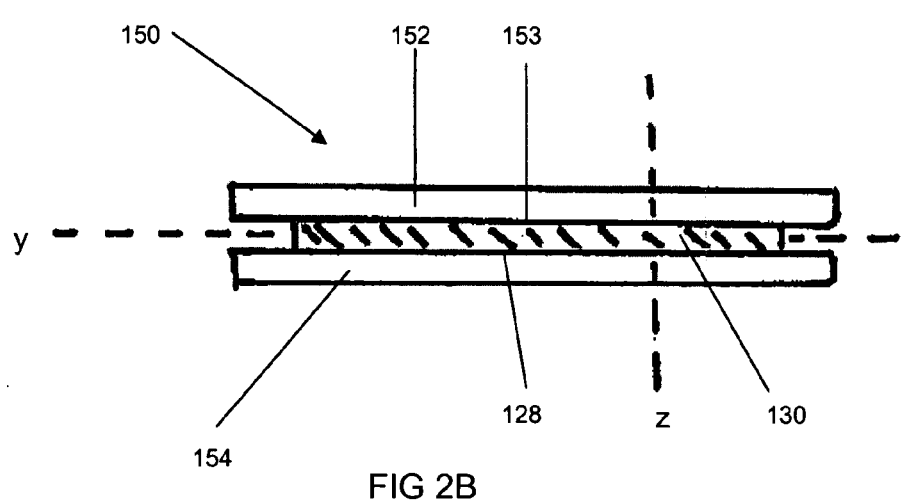
FIG. 2B is a cross-section view of FIG. 2A.

FIG. 2A shows an exemplary fastening system 150 according to certain embodiments. FIG. 2B shows a cross-sectional view of the exemplary fastening system 150 of FIG. 2A taken along line a-a. The fastening system 150 may include an engaging member 152 and a receiving member 154. The engaging member 152 may have an engaging surface 153 with a silicone-based adhesive 130 disposed thereon. The receiving member 154 may include a receiving surface 128 configured to receive the engaging surface 153 such that the engaging member and the receiving member can be joined together to engage the fastening system 150. When engaged, the engaging surface 153 may be in a planar face-to-face relation to the receiving surface 128.

The fastening system 150 may be generally planar with an x-axis and a y-axis, perpendicular to the x-axis, as shown in FIG. 2A. The fastening system 150 may have some caliper along a z-axis, shown in FIG. 2B, which is perpendicular to the plane formed by the x-axis and the y-axis. As will be appreciated in the description provided below, the fastening system 150 may experience a shear force generally directed along the x-axis or along any vector in the x-axis/y-axis plane. As will be further appreciated in the description provided below, the fastening system 150 may experience a peel force generally directed along the z-axis.

Suitable examples of engaging member 52, 152 and receiving member 54, 154 combinations include, but are not limited to adhesive engaging member and polymeric film receiving members, cohesive engaging members and cohesive receiving members, and adhesive engaging members and adhesive receiving members. In certain embodiments of the invention, a silicone-based adhesive 130 may be applied to a film or tape substrate, which is then permanently bonded to one or more layers of the disposable absorbent article to form an engaging member 52, 152. In certain embodiments, the silicone-based adhesive 130 may be applied to any suitable portion of the absorbent article, such as, for example, side panels, side margins, topsheet, backsheet, combinations thereof and the like. In still another example, a silicone-based adhesive 130 may be applied directly to a portion a diaper 20, enabling a user to join the engaging member 52 to the diaper portion. In certain embodiments the adherend or receiving member may comprise any suitable outer surface of the absorbent article, such as, for example, a backsheet.

One particularly suitable example of an engaging member 52, 152 and receiving member 54, 154 combination is an engaging member 52, 152 including a silicone-based pressure sensitive adhesive tape, such as, for example, S945 CL silicone tape available from Specialty Tapes Inc., Milwaukee, Wis. and a receiving member 54, 154 that includes a biaxially oriented polypropylene film (BOPP), such as, for example, KN 3829 available from Minnesota Mining and Manufacturing Company, St. Paul, Minn. It has been found that by combining an engaging member 52, 152 having a silicone-based adhesive with a suitable receiving member 54, 154, such as that described above, the noise levels produced by disengaging the engaging member 52, 152 from the receiving member 54, 154 may be reduced to less than 25 db; 15 dB; or even 10 dB when measured according to the Peel Noise Test described in more detail hereinbelow. Ideally, the noise level is 0 dB when the fastening system 50, 150 is disengaged.

In addition to being relatively quiet, the fastening system 50, 150 according to certain embodiments may also include a silicone-based adhesive that provides a tacky engaging surface 53, 153. The tacky surface may include all or only a portion of the engaging surface 53, 153. In addition, the tacky surface need not necessarily be provided by the silicone-based adhesive, but may be provided by a separate substance or material disposed on the engaging surface 53, 153, such as, for example, another adhesive. For some users, a tacky engaging surface 53, 153 may provide reassurance that the fastening system 50, 150 will remain engaged during the intended use of the article. For other users, a tacky surface may help the user place the article in a disposal configuration. For example, some disposable diapers include a fastening system that can be manipulated by a user in order to arrange the diaper in a relatively compact, folded-over, or rolled-up configuration and at least temporarily keep the diaper in such a configuration. By placing the diaper in a rolled-up configuration, for example, a user may reduce the amount of undesirable odor associated with a soiled diaper or ameliorate other undesirable aspects of the diaper disposal process (e.g., the diaper may be easier to carry, occupy less space in a waste disposal apparatus, or have a reduced likelihood of transferring bodily exudates to the skin or clothes of a caregiver or user).

As the tackiness of the engaging surface 53, 153 and/or receiving surface 128 increases, however, the likelihood that the tacky surface will become contaminated by surface contaminants, such as, for example, lint, dust, dirt, lotion and water, may also increase. Contamination of the engaging surface 53, 153 and/or receiving surface 128 may undesirably impact the performance of the fastening system 50, 150, for example, by decreasing bond strength or shortening the effective lifespan of the fastening system. One way to potentially reduce the level of contamination of the fastening system may be to provide a fastening system that includes an adherent with a relatively low surface energy. Examples of adherents exhibiting suitable surface energy include silicone-based adhesives with a surface energy of between 10 mN/m and 30 mN/m, for example, 25 mN/m.

Figure 2C:
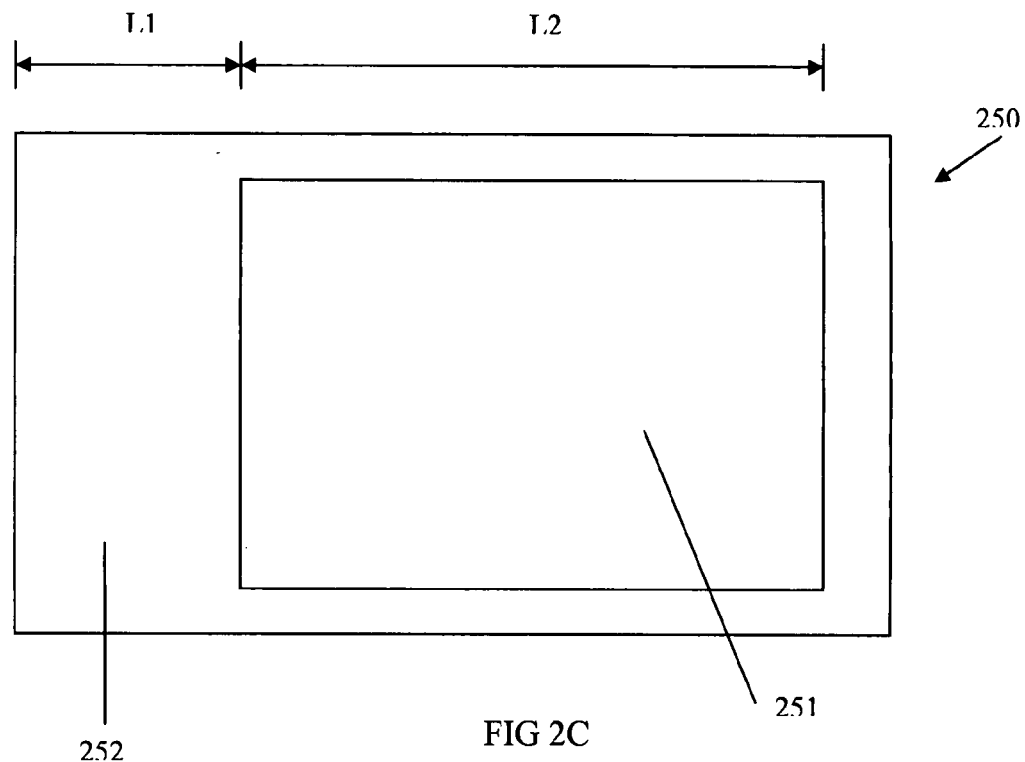
FIG. 2C is a plan view of an engaging member.

In certain embodiments, the fastening system may include an engaging member, such as the engaging member 250 shown in FIG. 2C, with a gripping portion 252 for enabling a user to grasp and manipulate the engaging member 250. The gripping portion has a length L1. Ideally, the gripping portion 252 will contain no adhesive. The engaging member 250 may also include an adhesive containing portion 251 having a length L2. In at least some fastening system designs, the adhesive containing portion 251 of the engaging member 250 is disposed adjacent the gripping portion 252. In some instances, the length L2 of the adhesive containing portion 251 may be greater than the length L1 of the gripping portion 252 to provide adequate adhesive strength for a particular use. As a result, users may contact the adhesive containing portion 251 with a finger or other object capable of transferring foreign matter onto the adhesive when fastening or refastening the article. Such contact may deposit contamination onto the adhesive and undesirably reduce its effectiveness.

Figure 2D:
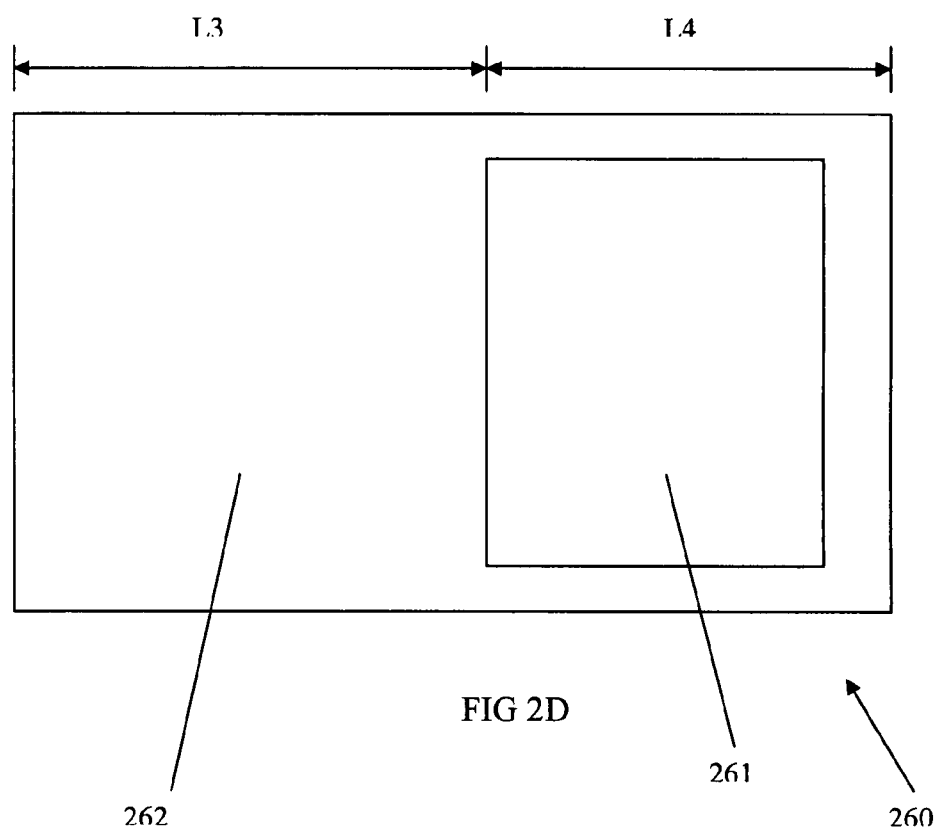
FIG. 2D is a plan views of an engaging member.

FIG. 2D shows an engaging member 260 having a gripping portion 262 with length L3 and an adhesive containing portion 261 with length L4. The engaging member 260 shown in FIG. 2D has a relatively shorter adhesive containing portion 261 than the adhesive containing portion shown in FIG. 2C. By increasing the length L3 of the gripping portion 262 relative to the length L4 of the adhesive containing portion of the engaging member (as shown in FIG. 2D), for example, from less than 12 mm to 12 mm or more, the likelihood of transferring foreign matter onto the adhesive during use of the fastening system may be reduced. In other embodiments, it may be desirable to modify the ratio of the length L3 of the gripping portion 262 to the length L4 of the adhesive containing portion 261 without changing the overall length of the engaging member 260. Suitable ratios of the gripping portion 262 to the adhesive containing portion 261 of the engaging member 260 include 1:1, 2:1, 5:1 or even 10:1. However, it is to be understood that any ratio where the potential for contamination of the adhesive containing portion 261 of the engaging member 260 is reduced is contemplated herein.

Optionally, when the fastening system 50, 150 includes a tacky surface and is not pre-engaged or otherwise configured to reduce contamination, it may be desirable to provide a fastening system that includes a covering material or protective component to at least partially cover the adhesive containing portion of the engaging member. The covering material or protective component may be removed from the engaging member by the manufacturer at any time during the manufacturing process or by a consumer of the end product. One suitable example of a covering is FSR 2000 coated substrate, available from GE silicone (Momentive Performance Materials Co.), Wilton, Conn.

Table 1 below illustrates comparative surface energies for various adhesives. The surface energy was measured according the Surface Energy Test described below. The column labeled description lists the type of adhesive and the product number. Samples 1-3 are silicone-based adhesive tapes available from Specialty Tapes, Inc., Milwaukee, Wis. Sample 4 is a rubber-based elastomer available from Dexco polymers, Houston, Tex. Sample 5 is a rubber-based adhesive available from Avery Dennison, Mentor, Ohio.

TABLE 1

| Sample | Description | Dispersive (mN/m) | Polar (mN/m) | Total (mN/m) |
|---|---|---|---|---|
| 1 | Silicone adhesive; 972ML-adhesive | 11.19 | 3.60 | 14.79 |
| 2 | Silicone Adhesive; S945CL | 9 | 3 | 12 |
| 3 | Silicone Adhesive; S599-adhesive | 20.13 | 0.00 | 20.13 |
| 4 | Rubber elastomer; Vector 4211 | 41.29 | 1.31 | 42.60 |
| 5 | Rubber adhesive; Avery F4408 | 34.87 | 0.04 | 34.92 |

In certain embodiments, a disposable absorbent article may be preformed by the manufacturer to create a pant. The term "pant," as used herein, refers to pre-engaged disposable garments having a waist opening and leg openings designed for infant or adult wearers. A pant may be preformed by any suitable method commonly known in the art. For example, the preforming may include joining the engaging member to the receiving member, making a nonrefastenable seam, fusion bonding, combinations thereof and the like, or any other suitable means known in the art. Suitable pants are disclosed in U.S. Pat. Nos. 5,246,433; 5,569,234; 6,120,487; 6,120,489; 4,940,464; 5,092,861; 5,897,545; and 5,957,908 and U.S. patent application Ser. No. 10/171,249, entitled "Highly Flexible And Low Deformation Fastening Device," filed on Jun. 13, 2002.

Consumers of disposable absorbent articles typically find it desirable to have a fastening system 50, 150 configured to keep the disposable absorbent article fastened during its intended use. For example, it may be desirable to provide the fastening system 50 of a disposable diaper 20 with sufficient strength and endurance to keep the diaper 20 positioned properly around the waist of a wearer when the wearer is physically active. In the case of a refastenable fastening system, however, consumers may desire the force required to disengage the refastenable fastening system ("disengagement force") to be less than 4.7 N/cm. In certain embodiments, consumers may desire a disengagement force of between 0.40 N/cm to 4 N/cm of force. In certain embodiments, the disengagement force may be between 0.8 N/cm to 3 N/cm of force. In certain embodiments, the disengagement force may be about 2 N/cm of force. All recited disengagement forces are generally in the z-direction and are measured according to the T-Peel Test, as described in the Test Methods section below. While a lower limit on the disengagement force is not necessarily required, it may be desirable. Otherwise, the fastening system 50 may experience an untimely, spontaneous separation.

It may be desirable that the fastening system 50, 150 exhibits suitable shear strength. Shear loads are generally applied along the x-axis. Two shear values may be considered: peak shear load (i.e., Dynamic Shear) and sustained load over time (i.e., static shear). With regard to integrity against a static, sustained load, the fastening system 50 may exhibit a Shear Hang Time of greater than 50 minutes; greater than 175 minutes; or even greater than 240 minutes. Ideally, the fastening system 50, 150 will exhibit a perpetual Shear Hang Time. The Shear Hang Time is measured according to the Shear Hang Time Test, which is described in the Test Methods section hereinbelow.

In certain embodiments, it may be desirable to provide a fastening system 50, 150 that exhibits suitable integrity against a dynamic load, as measured according to the Dynamic Shear Test described hereinbelow. Dynamic Shear values of at least 3.1 N/cm$^2$ or even at least 6.2 N/cm are non-limiting examples of suitable Dynamic Shear values.

In certain embodiments, an aged fastening system 50, 150 may not exhibit a substantial change in one or more functional characteristics as a result of aging. For example, after being subjected to an accelerated aging process (as defined herein), the fastening system 50, 150 according to certain embodiments may exhibit a Peel Noise value of less than 25 dB, a T-Peel Force value of less than 4.7 N/cm, a Shear Hang Time value of greater than 50 minutes, and/or a Dynamic Shear value of greater than 3.1 N/cm$^2$. In suitable embodiments capable of being subjected to an aging and/or accelerated aging process, the fastening system 50, 150 may exhibit a minimal change in T-Peel Force, Shear Hang Time and/or other performance characteristics.

In certain embodiments, it may be desirable to provide a refastenable fastening system that exhibits suitable performance characteristics after being subjected to one or more refastening events. Ideally, a refastenable fastening system exhibits no change in performance characteristics after being subjected to a refastening event. One example of a suitable performance characteristic includes a fastening system that exhibits a Peel Noise value of less than 25 dB; less than 15 dB; less than 10 dB; or ideally 0 dB after being subjected to at least a first refastening event. Other examples of suitable performance characteristics for refastenable fastening systems according to certain embodiments include disengagement forces of less than 4.7 N/cm; Shear Hang Times of greater than 50 minutes; and Dynamic Shear values of greater than 3.1 N/cm$^2$.

Table 2 illustrates comparative measurements of Peel Noise for various materials. The samples shown in Table 2 and the tables that follow were prepared and tested according to the respective test methods detailed hereinbelow. Additionally, the values listed in the tables were determined according to each respective test method. The samples in Table 2 include one mechanical fastener and three adhesive fasteners. Sample 1 is a PAMPERS SWADDLER brand disposable diaper that includes a hook and loop type mechanical fastener. Samples 2 and 3 are receiving member samples comprising polypropylene films available from the 3M Company, St. Paul, Minn. Sample 4 is a receiving member sample comprising a mono-layer polyethylene film. The polyethylene film was made on a Merritt-Davis Cast Film line, available from Davis-Standard, LLC, Pawcatuck, Conn. The mono-layer film had the following formulation: Dowlex 2045G (~85%) from Dow chemical, LD 129 (~10%) from Exxon Mobile, and Ampact 110573-B (~5%) from Ampacet Inc. The extrusion portion of the process was carried out at temperatures of between 400° F. and 480° F., with higher temperature at the die end. A film of 25.4 μm thickness was cast on cooled matte finish steel and rubber rolls, which were maintained at ~150° F., and ~100° F., respectively. The engaging member sample used to generate the data in the following table (except for the hook/loop sample) includes S945CL silicone tape, available from Specialty Tapes Inc., Milwaukee, Wis. One sample was tested for each of the values listed in Table 2.

TABLE 2

Fresh Peel Noise

| Sample No. | Sample Description | Fresh Peel (dB) | Avg. Re-fasten Peel (dB) |
|---|---|---|---|
| 1 | Hook/Loop Pampers Swaddler | 24.4 | 25.1 ± 1.2 |
| 2 | KN 3829 | 4.5 | 4.6 ± 1.9 |
| 3 | K0883 | 6.3 | 5.4 ± 0.5 |
| 4 | PE | 0.11 | 5.6 ± 3.9 |

Table 3 shows a measurement of the Peel Noise for an aged sample of KN 3829. One sample was tested.

TABLE 3

Aged Peel Noise

| Receiving Member Sample | Aged Peel (dB) | Avg. Re-fasten Peel (dB) |
|---|---|---|
| KN 3829 | 0.8 | 0.8 ± 0.4 |

Table 4 shows a measurement of the T-Peel force data from fresh samples of the listed materials. Four samples were tested for each material.

TABLE 4

Fresh T-Peel

| Receiving Member Sample | Fresh Peel (N/cm) | 1st Re-fasten Peel (N/cm) |
|---|---|---|
| KN 3829 | 0.49 ± 0.04 | 0.57 ± 0.04 |
| K0883 | 1.13 ± 0.04 | 0.52 ± 0.02 |
| PE | 1.15 ± 0.04 | 1.22 ± 0.06 |

Table 5 shows T-Peel force data from an aged sample of KN 3829.

TABLE 5

| | Aged T-Peel | |
| --- | --- | --- |
| Receiving Member Sample | Aged Peel (N/cm) | 1st Re-fasten Peel (N/cm) |
| KN 3829 | 1.69 ± 0.36 | 1.04 ± 0.24 |

Table 6 shows Shear Hang Time data for samples of the listed materials. Eight samples were tested for each material.

TABLE 6

| | Shear Hang Time | |
| --- | --- | --- |
| Receiving Member Sample | Fresh (minutes) | Aged (minutes) |
| KN 3829 | >240 | >240 |
| K0883 | >240 | |
| PE | >240 | |

Table 7 shows Dynamic Shear data for fresh samples of KN 3829. Six samples were tested.

TABLE 7

| | Fresh Dynamic Shear | |
| --- | --- | --- |
| Receiving Member Sample | Fresh (N/cm$^2$) | 1st Re-fasten (N/cm$^2$) |
| KN 3829 | 36.6 ± 1.4 | 35.8 ± 2.3 |

Table 8 shows Dynamic Shear data for aged samples of KN 3829. Eight samples were tested.

TABLE 8

| | Aged Dynamic Shear | |
| --- | --- | --- |
| Receiving Member Sample | Aged (N/cm$^2$) | 1st Re-fasten (N/cm$^2$) |
| KN 3829 | 22.3 ± 3.26 | 24.8 ± 2.95 |

Test Methods

For each of the sample preparations described below, the adherent should be handled with care to avoid contact with hands, skin, or other contaminating surfaces. Clean sheets of untreated paper may be used to protect adherent surfaces during the sample preparation. It is to be understood that some of the particular brands or models of instruments or materials listed in the methods below are exemplary. Where the particular instrument or material listed is not available, a suitable equivalent may be substituted where appropriate.

T-Peel Test

This method is used to determine the adhesive bond strength of an engaged fastening system.

Sample Preparation—The sample preparation for T-peel test will vary based on whether the material is available as a discrete web or is incorporated in a product.

Figure 3A:
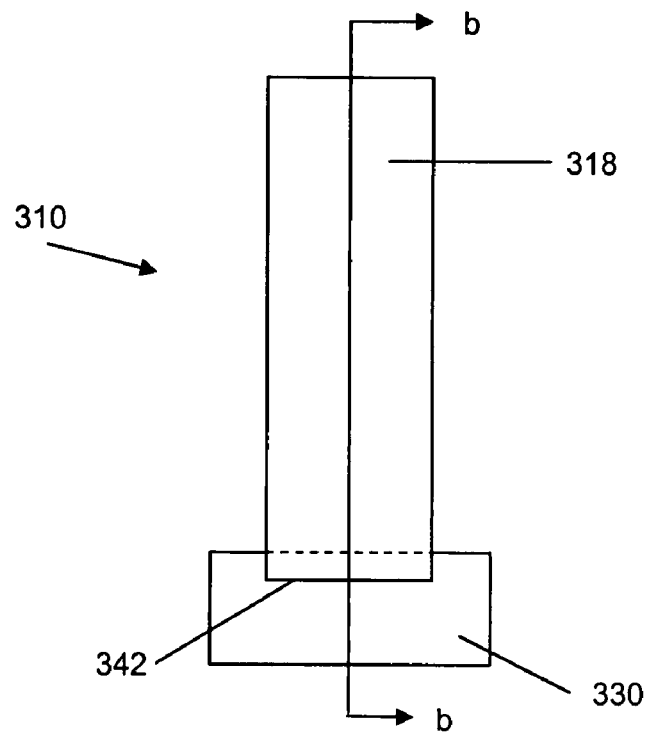
FIG. 3A is a plan view of a sample prepared according to the T-Peel Force Test method.
Figure 3B:
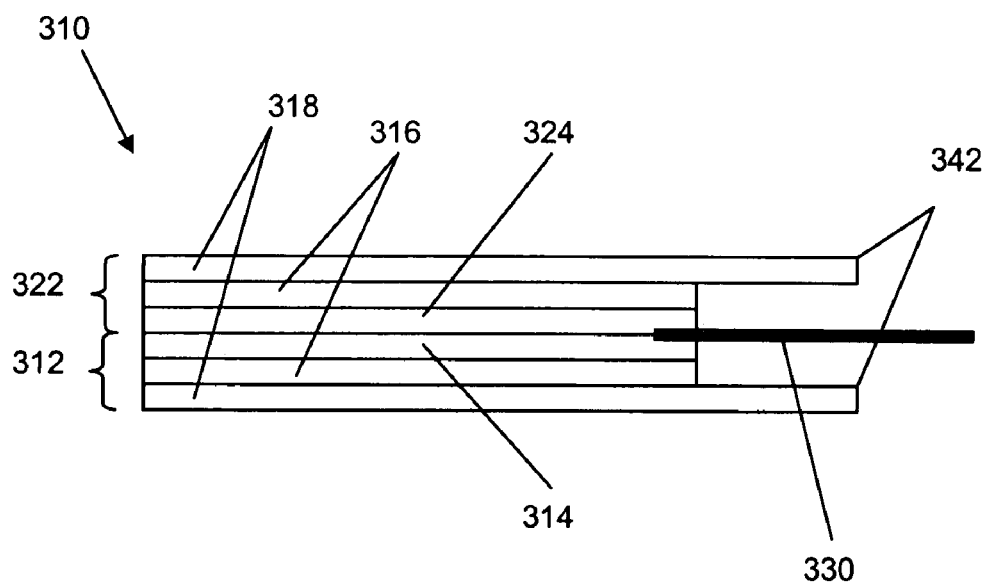
FIG. 3B is a cross-section view of FIG. 3A.

For materials as a discrete web: FIGS. 3A and 3B illustrate a sample 310 provided according to the directions below. FIG. 3B is a cross-sectional view taken along sectional line b-b of FIG. 3A.

Figure 4:
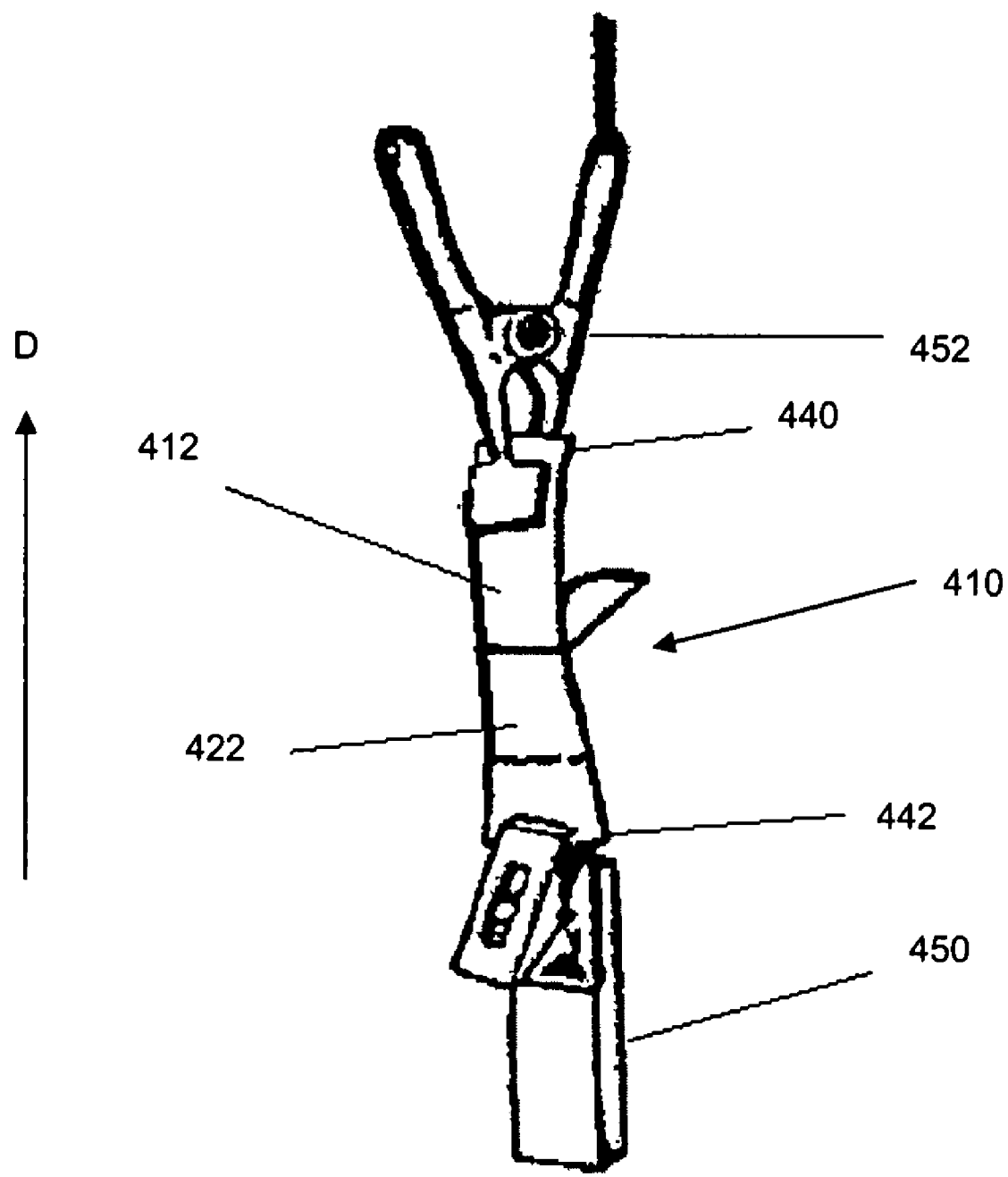
FIG. 4 is a perspective view of a sample being tested according to the T-Peel Force Test method.

Prepare the receiving sample 312 by joining a 2.54 cm wide×10.8 cm long piece of adherend 314 in a face-to-face relationship to a similarly sized piece of double-sided tape 316 such that the adherend and double-sided tape are substantially coterminous and wrinkle-free. Obtain a 2.54 cm×15 cm piece of 0.05 mm poly(ethylene terephthalate) (PET) film 318 and join the PET film 318 to the side of the double-sided tape 316 opposite the adherend 314 such that three edges of the PET 318 are aligned with three edges of the adherend/double sided tape laminate. One edge of the PET should extend 25 mm past the edge of the adherend/double-sided tape laminate, as shown in FIG. 4, in order to provide a gripping edge 342.

For the engaging sample 322, repeat the steps described above with regard to the receiving member using an appropriate adherent in place of the adherend After assembling the receiving sample 312 and the engaging sample 322, join the engaging sample 322 to the receiving sample 312 on a flat, clean, rigid surface. The resulting sample 310 should be substantially wrinkle-free. Ensure that the adherend 314 fully covers the adherent 324 and that the edges of the adherent 324 are substantially aligned with the edges of the adherend 314. If a sample 310 is to be aged, a small piece of release film 330, for example, a PP film coated with FSR 2000 coating available from GE Silicones, Waterford, N.Y., should be placed between the adherend 314 and the adherent 324, adjacent the gripping edge 342. The release film 330 should not be inserted more than 10% of the total bonded length of the sample 310 (e.g., a few millimeters). Roll the sample 310 with a 2 kg HR-100 ASTM 80 shore rubber-faced roller applying two full strokes (i.e., back and forth) at a speed of approximately 10 mm/sec. The bonded area of the sample 310 should be approximately 2.54 cm wide by 10.8 cm long. For "Fresh" T-peel force data, the sample 310 is tested within 10 minutes of bonding. The dimensions of the receiving and engaging members may vary from those listed, however, the effective bonding area should be used to normalize the resultant T-Peel force data per centimeter of bonded width.

For materials incorporated into a product and pre-engaged: Materials that are pre-engaged in the product are taken as having been aged and are not subjected to accelerated aging process. Cut the material from the product in order to isolate the adherend and adherent from the product. If the adherend and/or adherent are joined to other materials in a face-to-face configuration, maintain the configuration. Removal of the materials from the product should be done to preserve the integrity of the materials (e.g., adherend and adherent should not be permanently deformed or should not be debonded from each other). Before loading the samples for the T-peel test, the receiving and engaging surfaces should be separated approximately 1 to 5 mm to initiate peeling. The adherend sample and adherent sample should each have a portion that extends approximately 25 millimeters beyond the bonded portion of the samples similar to the proximal edge 342 described above and shown in FIG. 3B. If needed, an additional length of 0.05 mm thick PET film may be attached to the extended portion using double-sided tape. The T-peel test should be performed on the bonded materials as described in the method below. It should be appreciated that peel angle can affect the peel force. Therefore, during peeling, the peel angle should be kept as close to 180 degrees as possible. Furthermore, if the adherent or adherend exhibit elastomeric properties or deform when subjected to tensile forces less than 4.7 N/cm, the adherent or adherend must be backed with a similar sized sheet of 0.05 mm thick PET film in order to prevent stretching of the tested substrate.

If the product is not pre-engaged, cut the materials from the product and prepare a sample as if the materials were discreet webs. If the width of the material is less than 2.54 cm, then the weight (during aging) should be chosen such that pressure is 0.8 N/cm². The average load calculated in the T-peel force test should be normalized by the width of the fastener (in centimeters).

For Refastened samples: Any of the above mentioned samples may be refastenable. Such samples may be refastened and tested. The sample is debonded using the tensile tester per the test conditions described below for the T-peel test. The adherent and adherend are refastened according to the procedure in which they were originally attached (e.g., joined and rolled). After 1 minute of dwell time, perform the T-Peel Test. This is the first refastened T-Peel force. Repeat the procedure as needed to yield sequential refastened T-Peel forces (i.e., a second refastened T-Peel force, a third refastened T-Peel force, etc.).

Test Conditions—The T-Peel test method is performed in a controlled room at 22° C.±2° C. and RH 50%±10%. A tensile tester, for example, an Alliance RT/1 available from MTS Systems Corp., Eden Prairie, Minn., is used to perform the T-peel force measurements. The tensile tester should be interfaced with a computer loaded with software that controls the testing parameters, performs data acquisition and calculation, and provides graphs and data reports, for example, TestWorks™ version 4 Material Testing Software. Configure the tensile tester with a data acquisition speed of 10 Hz. Select an appropriate load cell (i.e., where the force to be measured is between 10% and 90% of the rated capacity of the load cell, typically a 100 N to 250 N max capacity load cell is sufficient) . Calibrate the instrument to an accuracy of at least 1%, ideally less than 0.1%, according to the manufacturer's instructions.

FIG. 4 illustrates an example of a test sample 410 in a tensile tester according to the T-Peel test method. The instrument shown in FIG. 4 has two grips: a stationary grip 450 and a movable grip 452. Grips 450, 452 that are wider than the sample 410 to be tested may be selected; typically, 5.08 cm wide grips are used. Configure the grips 450, 452 to clamp the sample 410 at the gripping edges 440, 442 of the receiving sample 412 and the engaging sample 422 such that the gripping force is substantially concentrated along a plane that is perpendicular to the direction D of testing stress. Set the distance between the lines of the gripping force (i.e., the gauge length) to 2.54 cm. Place the gripping edges 440, 442 of the sample 410 in the grips 450, 452 such that the receiving sample 412 or the adherend is placed in the movable grip 452 and the engaging member 422 or the adherent is placed in the stationary grip 450, as shown in FIG. 4. Configure the sample 410 to minimize the amount of slack in the receiving sample 412 and the engaging sample 422. Zero the load reading on the tensile tester.

The receiving sample 412 is separated from the engaging sample 422 using a crosshead speed of 305 mm/min. An average load is calculated as the average load between 25 mm and 88 mm displacement. For samples that do not meet the dimensions provided in the Sample Preparation section above, the average load is calculated from the loads acquired from the crosshead extension between 25% and 87.5% of the sample length. For example, if the sample is 15.24 cm long, the average load is calculated between 3.81 cm and 13.34 cm of crosshead extension. The average load is normalized to a width of 2.54 cm as follows: normalized load=average load÷initial bond width in centimeters.

Dynamic Shear Test

This method is used to determine the Dynamic Shear of an engaged fastening system.

Sample Preparation—The sample preparation for Dynamic Shear Test will vary based on whether the material is available as a discrete web or is incorporated in a product.

Figure 5A:
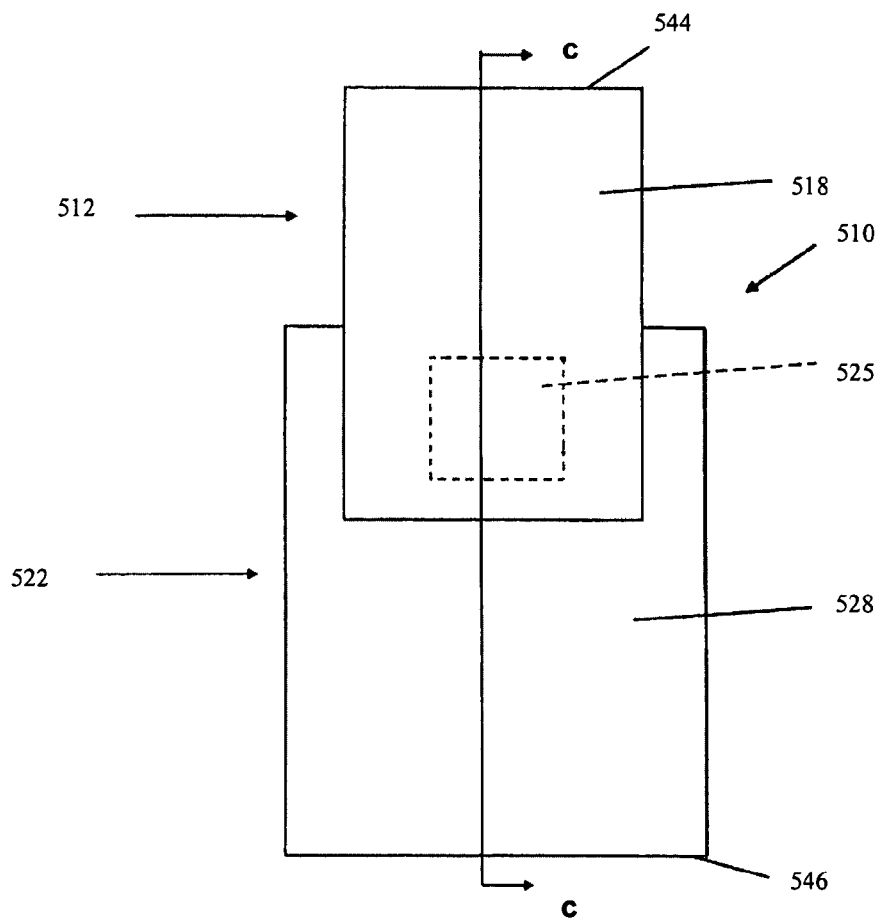
FIG. 5A is a plan view of a sample prepared according to the Dynamic Shear Test method.
Figure 5B:
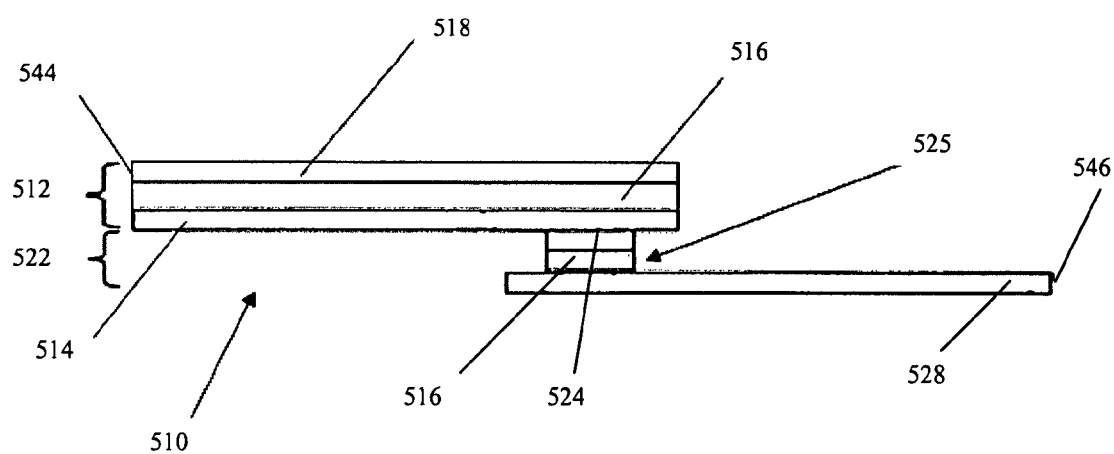
FIG. 5B is a cross-section view of FIG. 4A.

For materials as a discrete web: FIGS. 5A and 5B illustrate a sample 510 formed according to the method provided below. FIG. 5B is a cross-sectional view taken along sectional line c-c of FIG. 5A.

In order to provide a receiving sample 512 having a distal edge 544, an adherend 514 is resized using cutting dies to create rectangular receiving samples with the dimensions of 3.5 cm wide and 20 cm long. The adherend 514 is backed with a like sized piece of PET film 518 using double sided tape 516 to form receiving sample 512 (see T-peel Force Test method).

For the engaging sample 522, an approximately 2.54 cm×2.54 cm piece of the adherent 524 is bonded in a face-to-face relationship to a similarly sized piece of double-sided tape 516 to form engaging laminate 525. The adherent 524 and double-sided tape 516 are joined to be substantially coterminous. The adherent 524 is to be wrinkle free. It should be appreciated that the engaging laminate 525 can be created with larger sized materials and then resized to 2.54 cm×2.54 cm. The other side of the double-sided tape 516 is bonded to a 5.08 cm×15.24 cm stainless steel plate 528 such that one side of the engaging laminate 525 is approximately 1.27 cm from a 5.08 cm wide edge of plate 528. The plate 528 has a distal edge 546 opposite the edge adjacent to the laminate 525. The engaging laminate 525 should be centered along the width of the plate 528.

The receiving sample 512 is bonded with the engaging sample 522 so as to avoid wrinkles and so that the adherend 514 fully covers the adherent 524. The edges of the receiving sample 512 and the edges of the engaging sample 522 are substantially parallel to each other. The receiving sample 512 is bonded to the engaging sample 522 such that the receiving sample 512 extends beyond the plate 528. The sample 510 is configured such that the distal edge 544 of the receiving sample 512 and the distal edge 546 of the plate 528 are opposite one another. The sample 510 is rolled with a 2 kg HR-100 ASTM 80 shore rubber-faced roller. Two full strokes (i.e., back and forth) are applied to the sample at a speed of approximately 10 mm/sec. The bonded area should be approximately 2.54 cm by 2.54 cm. If the dimensions of the receiving and engaging members vary from those disclosed herein, the effective bonding area should be used to normalize the resultant Dynamic Shear recorded per square centimeter of bonded area.

Materials incorporated into a product and pre-engaged: The steps for preparing a pre-engaged sample incorporated into a product are the same as for the T-peel test with the following exceptions. The adherent is attached to a 5.08 cm×15.24 cm stainless steel plate to form an engaging sample. The adherend (already engaged with the adherent) should have a distal edge that extends at least 25 millimeters from the bonded portion of the adherent and adherend such that the distal edge can be easily inserted into the grip of a test instrument. The Dynamic Shear Test should be performed on the bonded materials as described in the method below.

If the product is not pre-engaged, the materials are cut from the product and sample preparation would be similar to the method presented above for a sample in a film form.

Refastened samples: Any of the above mentioned samples may be refastenable. A refastened sample is prepared by debonding the sample using the tensile tester as outlined in the Dynamic Shear Test method below. The adherent and adherend are refastened in a configuration substantially similar to the configuration in which they were originally attached while avoiding wrinkles. The resample is configured such that the distal edge of the receiving sample is remote from the distal edge of the plate.

The refastened sample is rolled with a 2 kg HR-100 ASTM 80 shore rubber-faced roller. Two full strokes are applied to the sample at a speed of approximately 10 mm/sec. The refastened sample is allowed to sit for 1 minute of dwell time. Debonding and refastening may be repeated to yield a second refastening, third refastening, etc. The refastened sample may be tested to provide a Dynamic Shear value.

Figure 5C:
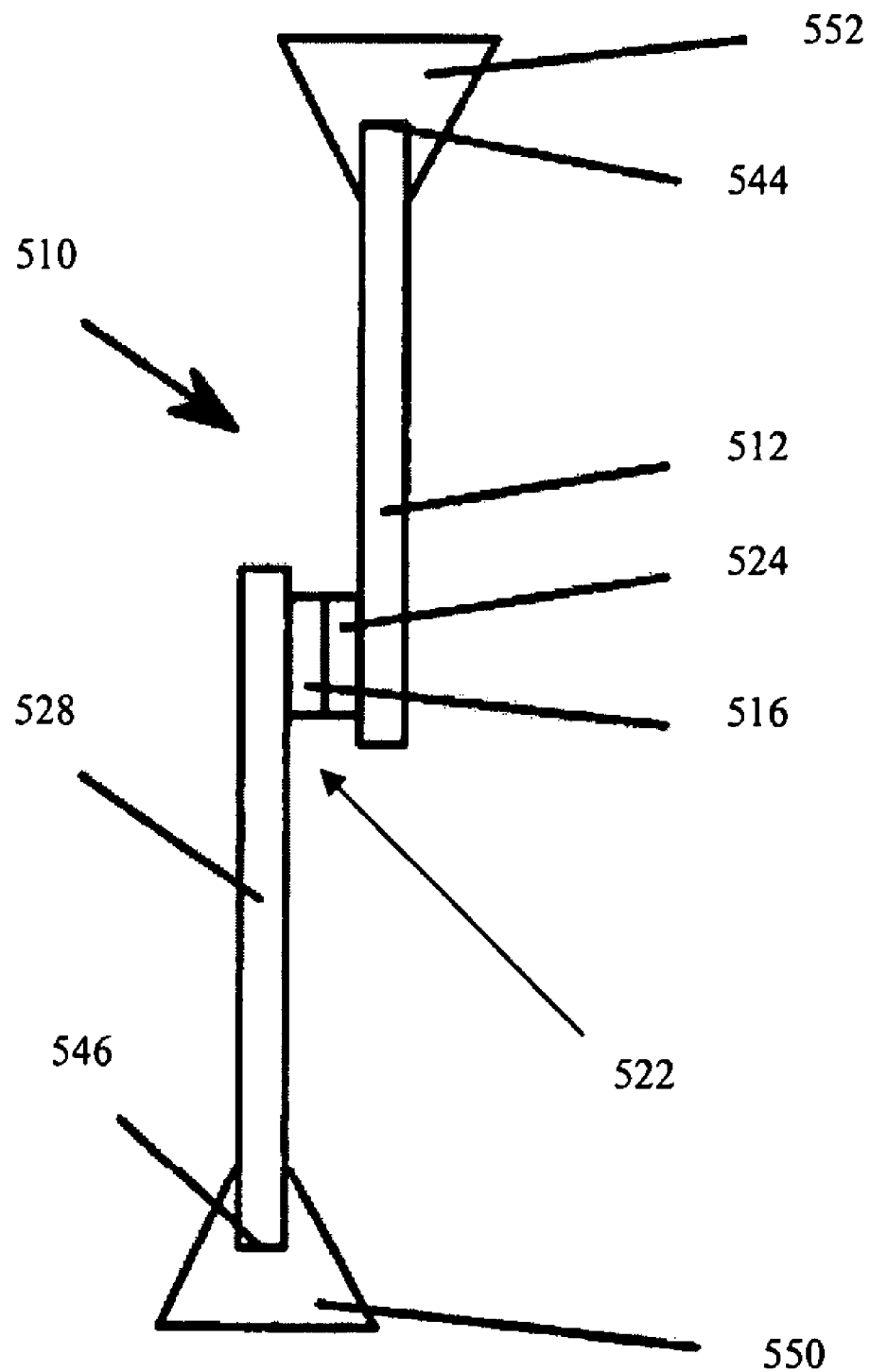
FIG. 5C is a perspective view of a sample during a Dynamic Shear Test.

Test Conditions—The Dynamic Shear Test method is performed in the same environmental conditions and with the same tensile tester as disclosed in the T-Peel Test. FIG. 5C shows the sample 510 mounted in two grips 550, 552 of the tensile tester. The grips are selected to be wider than the adherend 514 or adherent 524, typically 2.54-5.08 cm, and to concentrate the entire gripping force along a plane perpendicular to the direction of testing stress. The distal edge 546 of the metal plate 528 is mounted into the stationary grip 550. The distal edge 544 of the receiving sample 512 is mounted into the movable grip 552. Mount the sample in the grips 550, 552 so that there is a minimum amount of slack in the sample and the load measured is less than 0.5 N. Select the distance between the lines of the movable grip 552 and the proximate edge of the bond site to be 3.3 cm. Zero the load reading on the instrument.

The receiving sample 512 is separated from the engaging sample 522 using a crosshead speed of 305 mm/min until the two samples are completely disengaged or one of the samples fails (e.g., the engaging sample 522 tears, receiving sample 512 tears, or the sample 510 debonds at an interface other than of that between the engaging sample and the receiving sample). If the sample 510 fails at any location other than the interface between the adherend and adherent prior to reaching a maximum load of at least 3.1 N per $cm^2$ of bond area, the data is to be discarded and another sample must be run. If the sample fails at the interface other than adherend/adherent interface at load more than 3.1 N per $cm^2$ of bond area, then the data is discarded. If the sample does not disengage below 38.75 N per $cm^2$ of bond area, the Dynamic Shear of the bond is considered 38.75 N per $cm^2$ of bond area for calculation purposes. To generate refastening data on such samples, the samples are separated manually.

The Dynamic Shear is calculated as follows: Dynamic Shear=measured load÷bonded area in centimeters squared.

Shear Hang Time Test

This method is used to determine the shear resistance, measured in time, of the bond formed between an adherent and an adherend when the bond is subjected to a load in controlled temperature environments. This test is derived from FINAT Test Method No. 8, the European Association for the Self Adhesive Tape Industry (AFERA) Test Method No. 4012, and ASTM-D Test Method No. 6463.

Sample Preparation—The sample preparation for Shear Hang Time test will vary based on whether the material is available as a discrete web or is incorporated in a product.

Figure 6A:
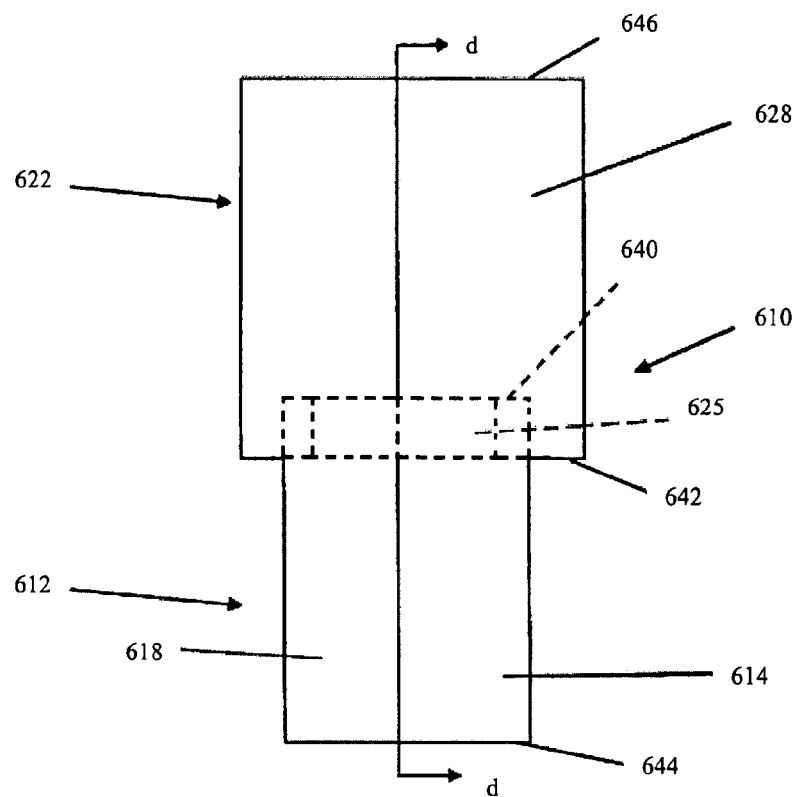
FIG. 6A is a plan view of a sample prepared according to the Shear Hang Time Test method.
Figure 6B:
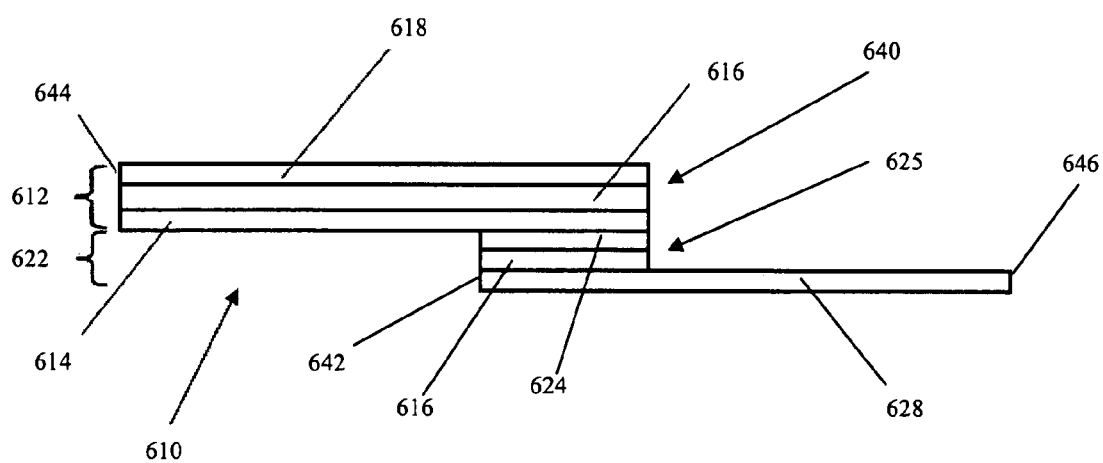
FIG. 6B is a cross-section view of FIG. 6A.

For materials as a discrete web: FIGS. 6A and 6B illustrate a sample 610 formed according to the method provided below. FIG. 6B is a cross-sectional view taken along sectional line d-d of FIG. 6A.

For a receiving sample 612 having a proximal edge 640 and a distal edge 644, an adherend 614 is resized using cutting dies to create a rectangular sample with the dimensions of 3.5 cm×7.5 cm. The adherend 614 is backed with a like sized backing sheet 618 of PET film using double-sided tape 616. Position and size the backing sheet 618 so as to not interfere with the adherend to adherent interface.

For the engaging sample 622, an approximately 1.3 cm×2.54 cm piece of an adherent 624 is bonded in a face-to-face relationship to a similarly sized piece of double-sided tape 616 to form engaging laminate 625. The adherent 624 is to be wrinkle free. Join the other side of the double-sided tape 616 to a 3"×2" test panel 628 having a proximal edge 642 and a distal edge 646. Bond the double-sided tape 616 adjacent the proximal edge 642 of the test panel 628. The test panel 628 is ideally made from steel (ASTM A66 specification). Alternatively, the test panel 628 may be made from corrugated cardboard panel having a thickness of at least 3-4 mm and a substantially planar surface. The adherend 614 is bonded onto the adherent 624. The sample 610 is then rolled with a 2 kg HR-100 ASTM 80 shore rubber-faced roller. Two full strokes (i.e., back and forth) are applied to the sample 610 at a speed of approximately 5 mm/sec. The bonded area should be approximately 2.54 cm×1.3 cm. If the dimensions of the receiving and engaging members vary from those listed above, the sample should be resized to yield a bonded area of 2.54 cm×1.3 cm.

Materials incorporated in a product: Materials that are pre-bonded in the product are taken as having been aged and therefore, require no additional aging. Cut the material from the product so as to isolate the adherend and adherent from the product. If the adherend and/or adherent are joined to other materials in a face-to-face configuration, maintain the configuration. Removal of the materials from the product should be done to preserve the integrity of the materials (e.g., adherend and adherent should not be permanently deformed and should not be debonded from each other). The adherent is attached via double-sided tape to test panel to form an engaging sample. The receiving sample (already engaged with the adherent 624) should have a distal edge that extends at least 50 millimeters from the bonded portion of the adherent 624 and adherend such that the distal edge can be easily folded over to form a loop. If the distal edge does not extend at least 50 mm, an additional length of 0.05 mm PET film may be attached to the distal edge using double sided tape. The shear hang test should be performed on the bonded materials as described in the method below.

If the product is not pre-engaged, the materials are cut from the product and sample preparation would be similar to the method presented above for a sample in a film form.

Test Conditions—The sample 610 is prepared at ambient room conditions (e.g., 22° C.±2° C. and RH 50%±10%). The sample 610 is brought into a temperature chamber immediately prior to the commencement of testing. The time between introduction of the sample 610 into the temperature chamber and commencement of testing is to be less than 5 minutes. The test is conducted in a 37.5° C.±2° C. controlled temperature chamber or oven. Suitable instruments for this test are the RT10 or RT30 available from ChemInstruments Inc, Fairfield, Ohio or any apparatus having a rack or jig capable of holding a test plate within 0° to 2° of vertical. The time is measured by an automated timer capable of reading to the nearest minute.

Figure 6C:
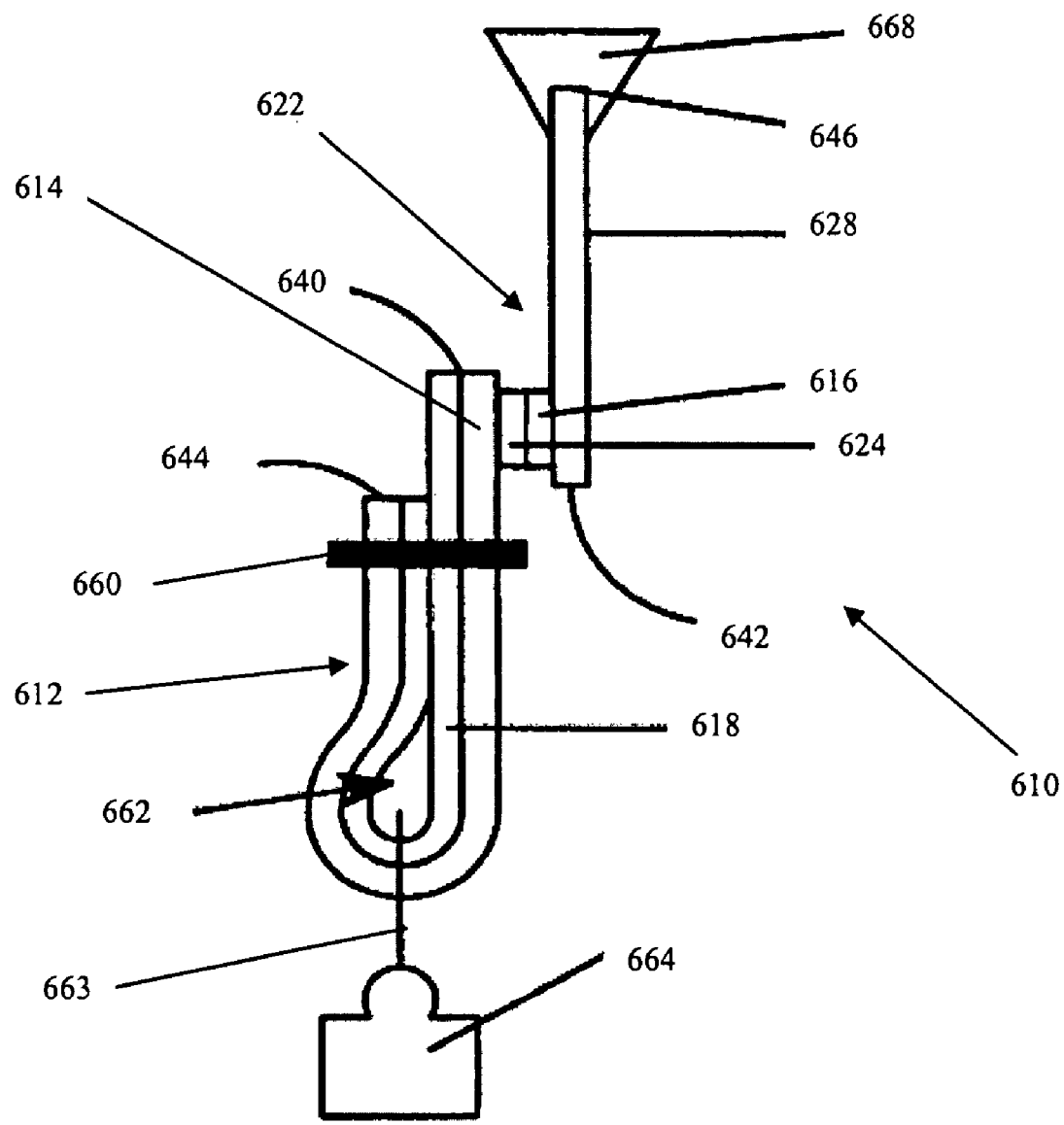
FIG. 6C is a perspective view of a sample during a Shear Hang Time Test.

FIG. 6C illustrates an example of a sample 610 tested according to the Shear Hang Time Test method. The distal edge 644 of the adherend receiving sample 612 is folded onto itself and affixed with a staple 660 to form a loop 662. The distal edge 646 of the engaging sample 622 is placed into the rack 668 so that the receiving sample 612 hangs downwards. Attach a 1 kg weight 664 to the free end of the receiving sample 612 by a any suitable attachment means, such as, for example, by hooking or otherwise engaging a string 663 through the loop 662 formed in the adherend 614. The timer is started once the weight 664 hangs freely from the receiving sample 612. The time required for debonding of the adherend 614 and the adherent 624 is recorded (i.e., the receiving member 612 separates and falls from the engaging member 622). The test can be manually stopped if the sample remains bonded beyond a prescribed time period (240 minutes).

If the sample fails at a time less than specified within this disclosure for some reason other than separation of the interface between the engaging sample and the receiving sample (e.g., the engaging sample tears, receiving sample tears, or the sample debonds at an interface other than of that between the engaging sample and the receiving sample), discard the data and run another sample using a backing material to prevent the sample from tearing and/or using a stronger double sided tape to prevent separation at interfaces other than between the engaging sample and the receiving sample. To get an average Shear Hang Time, a total of 8 good samples are run. If the sample survives beyond 240 minutes, then its Shear Hang Time is considered 240 minutes for the average Shear Hang Time calculation.

Peel Noise Test: This method is used to determine peel noise of engaged fastening system.

Materials:
Sound Meter (VWR Brand, Cat. #: 12777-836, S/N #: 51095069)
Lexan Board (6" wide×6" long×¼" thick)
Double Sided Tape (3M Double Coated Tape 9589, 5.08 cm wide, HDPE Carrier) Receiving Member Film
Sample Preparation—The sample preparation for Peel Noise Test will vary based on whether the material is available as a discrete web or is incorporated in a product.

Figure 7A:
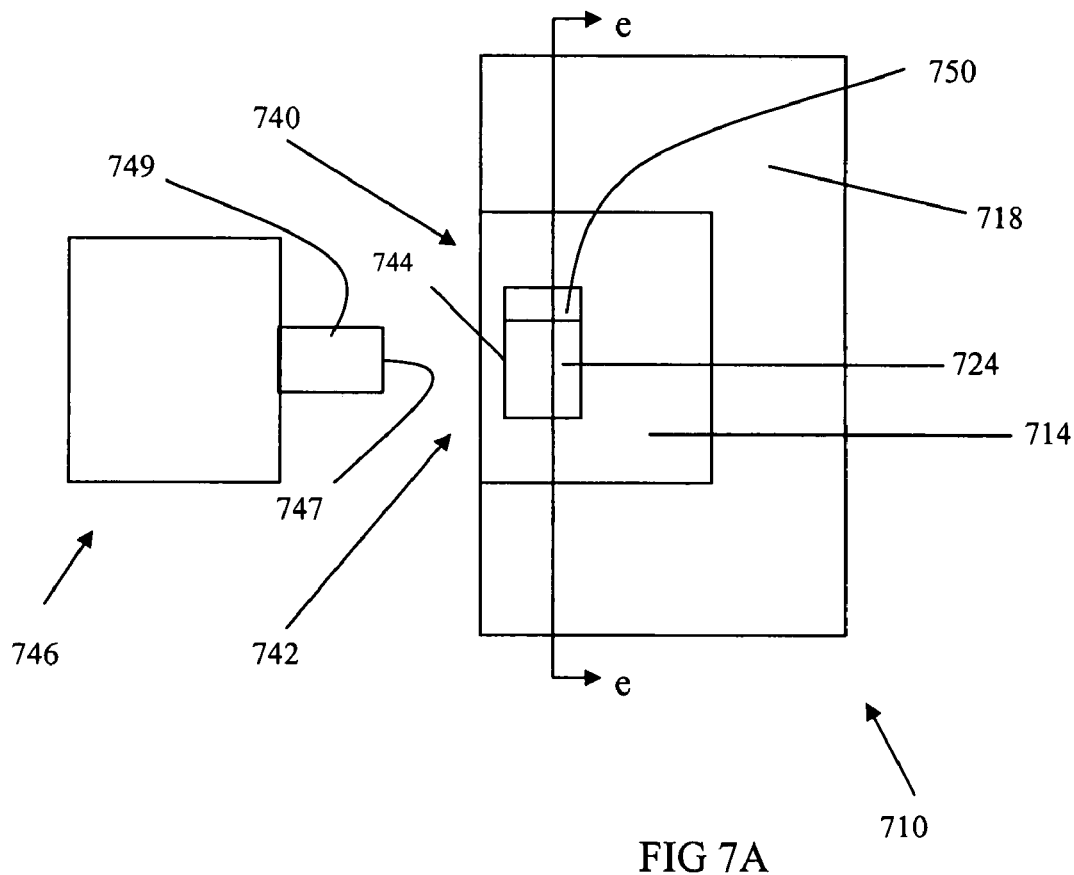
FIG. 7A is a plan view of an exemplary setup according to the Peel Noise Test method.
Figure 7B:
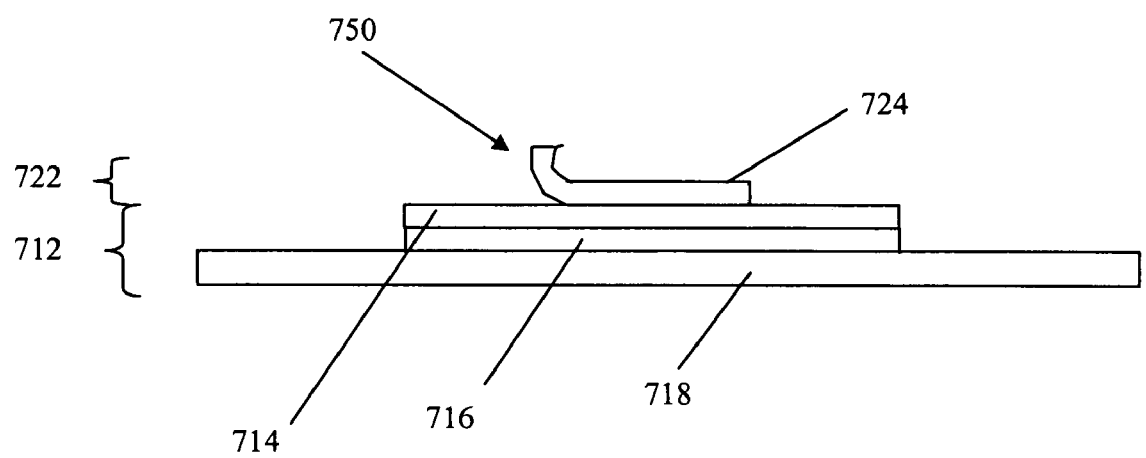
FIG. 7B is a cross-section view of a FIG. 7A.

For materials as a discrete web: FIGS. 7A and 7B illustrate a bonded sample 710 formed according to the directions provided below. FIG. 7B is a cross-sectional view taken along sectional line e-e of FIG. 7A.

For the receiving sample 712, bond a 5.08 cm×5.08 cm piece of an adherend 714 in a face-to-face relationship to a similarly sized piece of double-sided tape 716 such that the adherend 714 and double-sided tape 716 are substantially coterminous and wrinkle-free. The receiving sample 712 may be created with larger sized materials and then resized to 5.08 cm×5.08 cm. Bond the other side of the double-sided tape 716 to an approximately 15.24 cm×15.24 cm piece of 6.4 mm thick Lexan board 718, keeping the longitudinal edge 740 of the receiving sample 712 aligned with the longitudinal edge 742 of the Lexan board 718.

For the engaging sample 722, cut a 1.9 cm wide×2.54 cm long piece of an adherent 724 and fold down a gripping edge 750 for gripping purposes (~64 mm), so that a 1.9 cm×1.9 cm area of adhesive was exposed.

Bond the engaging sample 722 to the receiving sample 712 on a flat, clean, rigid surface such that the adherend 714 fully overlaps the adherent 724, and avoid wrinkling the sample 710. The longitudinal edge 744 of engaging sample 722 should be substantially parallel with the longitudinal edge 740 of the receiving sample 712 and less than 1.27 cm from the longitudinal edge 740 of the receiving sample 712. The decibel meter 746 is placed so that the proximal edge 747 of the decibel meter microphone 749 is 1.27 cm from the longitudinal edge 744 of the engaging sample 722. If bonded sample 710 is to be aged, a small piece of release film (such as a PP film coated with FSR 2000 coating available from GE Silicones, Waterford, N.Y.) is placed between the adherend 714 and the adherent 724. The release film should not be inserted more than a few millimeters between the adherend 714 and the adherent 724 (i.e., no more than 10% of the total bonded length). The sample 710 is bonded under moderate fingertip pressure (~104 g/cm$^2$). The bonded area should be approximately 1.9 cm×1.9 cm. For "Fresh" T-peel data, the bonded sample 710 is tested immediately (i.e., within 10 minutes of bonding). For "Aged" T-peel data, the bonded sample 710 is subjected to an accelerated aging process at a temperature of 60° C. and a continuous pressure of 0.8 N/cm$^2$ for 3 days prior to testing.

Materials incorporated in a product: Attach the open surface of the receiving members of an engaged sample to a Lexan board using double sided tape in such a way that the proximal end 747 of the microphone 749 can be placed at 1.27 cm from the longitudinal edge of the engaging member. Before running the Peel Noise test, the receiving member and engaging member surfaces should be separated approximately 1-5 mm to initiate the peeling. The Peel Noise test should be performed on the bonded materials as described in the method below. A skilled artisan should recognize that peel angle can affect the peel noise. During peeling, the peel angle should be maintained between 90 and 180 deg. Furthermore, if the adherent is elastomeric or is weaker than the bond strength up to 4.7 N/cm, the adherent may be backed with a similar sized sheet 0.05 mm PET film in order to prevent stretching of the substrate.

If the product is not pre-engaged, the materials are cut from the product and sample preparation would be similar to the method presented above for a sample in a film form. For aged Peel Noise data, these samples would need aging after engagement.

Refastened samples: Any of the above mentioned bonded samples 710 (e.g., materials in a discrete film form or material in a product) may be refastened. The bonded sample 710 is debonded following the test conditions for the Peel Noise Test as provided for below. The adherent 724 and adherend 714 are refastened in a configuration substantially similar to the configuration in which they were originally attached while avoiding wrinkles. The refastened sample is rolled with a 4.5 pound (2 kg) HR-100 ASTM 80 shore rubber-faced roller. Two full strokes (i.e., back and forth) are applied to the sample at a speed of approximately 10 mm/sec (i.e., rolling should take approximately 40 seconds. After 1 minute of dwell time, the Peel Noise Test is performed. This re-fastening and re-peeling process is repeated four times to get average re-fastening noise data.

Test Conditions—The Peel Noise test method is performed in a controlled room, which has low ambient noise (~70 dB or less). An average ambient peak noise level for the specific room on the day of testing is determined by taking several measurements (10 points using the method described below) and averaging them. The following procedure illustrates the measurement when using this instrument.

The decibel meter 746 is configured with a C filter, which allows the meter 746 to be sensitive to frequencies from 30 Hz to 10 kHz. The decibel meter 746 is set to measure low sound range, which is 35 to 100 dB. The distance between the tip of decibel meter microphone 747 and the longitudinal edge of the engaging sample 744 is set to 1.27 cm. The microphone 749 is centered in the peel area. The engaging sample 722 is separated from the receiving sample 724 by hand at a typical rate of removal (e.g., approximately 14 cm/sec) and the peak noise level measured by the decibel meter 746. The engaging member 722 is then reattached to the receiving member 724 in the manner described in the refastened sample section of this test method and peeled 4 more times with each peak noise level being recorded. The noise levels from each of the four re-fastening/re-peeling measurements are averaged together to provide the re-peel data. Subtract the ambient noise level from each of the 1st peel data and the re-peel data to determine the amount of noise above baseline that was associated with the different fastening systems.

Surface Energy Test:

Sample Preparation: Films are mounted to glass slides using double-sided tape to provide a flat, smooth surface.

Materials: Millipore UltraPure water and 99.9%+diiodomethane (available from Aldrich) are used as test solvents.

Procedure:

Accurate and precise volumes of the Millipore UltraPure water and diiodomethane are delivered under ambient temperature and relative humidity to the surface of a slide using a syringe pump. The maximum drop volume that can be suspended from the syringe needle is used for subsequent drops. Approximately 7 µL and 1.4 µL drop volumes are used for water and diiodomethane, respectively. The pendant drop is brought into contact with the film's surface and the solvent drop detaches from the syringe needle to wet the surface. An FTA200 Contact Angle Analyzer (Available from First Ten Angstroms ("FTA"), Portsmouth, Va.) equipped with imaging software (also from FTA) is used to collect an image of the drop in ≦10 seconds after the drop is placed onto the film's surface. The FTA software determines the contact angle of the solvent drop via drop shape analysis. Approximately 3-8 drops are used for each with each solvent to ensure that any surface heterogeneity is represented. The polar and dispersive components of the surface energy of the solvent are calculated from the contact angles of the substrate and the polar and dispersive surface energy using the Fowkes Method shown below in Data Analysis.

Data Analysis:

The polar and dispersive components of the surface energy are calculated from the substrate's contact angles and the solvents' polar and dispersive surface tensions (shown below) using the primary Fowkes equation. Table 9 shows the standard values for the polar and dispersive components of water and Diiodomethane.

TABLE 9

| Solvent | Polar Component (mJ/m$^2$) | Dispersive Component (mJ/m$^2$) | Total Surface Tension (mJ/m$^2$) |
|---|---|---|---|
| Water | 26.4 | 46.4 | 72.8 |
| Diiodomethane | 0 | 50.8 | 50.8 |

The primary Fowkes equation:

$$(\sigma_L^D \gamma s)^{0.5} + (\sigma_L^P \gamma s^P)^{0.5} = (\sigma_L(\cos\theta + 1))/2$$

Where, $\sigma_L^D$=dispersive surface tension of test solvent, $\sigma_L^P$=polar surface tension of test solvent, $\sigma_L$=total surface tension of test solvent, $\gamma s^D$=dispersive surface energy of substrate (or film), $\gamma s^P$=polar surface energy of substrate (or film), $\theta$=contact angle measured using the method described above.

The primary Fowkes equation may be rewritten as:

$$(\sigma_L(\cos\theta+1))/(2(\sigma_L^D)^{0.5}) = (\gamma s^P)^{0.5}(\sigma_L^P/\sigma_L^D)^{0.5} + (\gamma s^D)^{0.5}$$

The equation may be plotted as y=mx+b for the two solvents in Table 9 to calculate the film's unknown polar and dispersive surface energies where:

$$y=(\sigma_L(\cos\theta+1))/(2(\sigma_L^D)^{0.5}),\ m=(\gamma s^P)^{0.5},\ x=(\sigma_L^P)^{0.5}/(\sigma_L^D)^{0.5},\ \text{and}\ b=(\gamma s^D)^{0.5}$$

The slope m is used to calculate polar surface energy of substrate (adhesive in this case) and intercept b calculates dispersive component of substrate surface energy. The sum of polar and dispersive component gives total surface energy of substrate.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to certain embodiments. To the extent that any meaning or definition of a term in this document conflicts with any meaning or definition of the same term in a document incorporated by reference, the meaning or definition assigned to that term in this document shall govern.

While particular embodiments have been illustrated and described, it would be obvious to those killed in the art that various other changes and modifications can be made without departing from the spirit and scope of the invention. It is therefore intended to cover in the appended claims all such changes and modifications that are within the scope of this invention.

What is claimed is:

1. A refastenable quiet adhesive fastening system for use with a disposable absorbent article, the quiet adhesive fastening system comprising:
   a. one or more engaging members, each engaging member comprising an engaging surface and a gripping portion that contains no adhesive;
   b. one or more receiving members, each receiving member comprising a receiving surface;
   c. a silicone-based adhesive disposed on at least one engaging member;
   d. at least one receiving member being configured to receive at least one engaging member such that when the engaging surface of the engaging member is brought into contact with the receiving surface of the receiving member the silicone-based adhesive refastenably joins the engaging member and the receiving member together with an adhesive bond; and
   e. at least one of a fresh Peel Noise and an aged Peel Noise value of less than 25 dB according to the Peel Noise Test when the fastening system is disengaged where the adhesive bond has at least one of a fresh Shear Hang Time and an aged Shear Hang Time of greater than 50 minutes according to the Shear Hang Time Test.

2. The quiet adhesive fastening system of claim 1, further comprising at least one of a fresh Peel Noise and aged peel noise value of less than 15 dB according to the Peel Noise Test.

3. The quiet adhesive fastening system of claim 1, wherein the adhesive bond has at least one of a fresh Shear Hang Time and an aged Shear Hang Time of greater than 240 minutes according to the Shear Hang Time Test.

4. The quiet adhesive fastening system of claim 1, wherein the adhesive bond has at least one of a fresh Dynamic Shear and an aged Dynamic Shear of greater than 3.1 N/cm$^2$ according to the Dynamic Shear Test.

5. The quiet adhesive fastening system of claim 1, wherein the silicone-based adhesive has a surface energy of less than 30 mN/m according to the Surface Energy Test.

6. The quiet adhesive fastening system of claim 1, wherein the silicone-based adhesive has a surface energy of less than 25 mN/m according to the Surface Energy Test.

7. The quiet adhesive fastening system of claim 1, wherein the adhesive bond has at least one of a fresh T-Peel Force and an aged T-Peel Force of less than 4.7 N/cm according to the T-Peel Test.

8. The quiet adhesive fastening system of claim 1, wherein the adhesive bond has at least one of a fresh T-Peel Force and an aged T-Peel Force of between 0.4 N/cm and 4.0 N/cm according to the T-Peel Test.

9. The quiet adhesive fastening system of claim 1, wherein the fastening system has a Peel Noise value of less than 25 dB after a first refastening event according to the Peel Noise Test.

10. The quiet adhesive fastening system of claim 1, wherein the fastening system has a Shear Hang Time of greater than 100 minutes after a first refastening event according to the Shear Hang Time Test.

11. The quiet adhesive fastening system of claim 1, wherein the fastening system has a Dynamic Shear after a first refastening event of greater than 3.1 N/cm$^2$ according to the Dynamic Shear Test.

12. The quiet adhesive fastening system of claim 1, wherein the fastening system has a T-Peel Force after a first refastening event of between 0.4 N/cm and 4.7 N/cm according to the T-Peel Test.

13. A disposable absorbent article comprising:
   a. a topsheet, a backsheet, and an absorbent core disposed therebetween; and
   b. a quiet adhesive fastening system according to claim 1, wherein the fastening system is configured to enable a user to overlap the first engaging member and the second engaging member.

14. The absorbent article of claim 13, wherein the fastening system enables a user to place the absorbent article in a disposal configuration.

15. The absorbent article of claim 13, wherein at least one of the first and second engaging members is configured to have a receiving surface opposite the engaging surface.

* * * * *

UNITED STATES PATENT AND TRADEMARK OFFICE
CERTIFICATE OF CORRECTION

| | | |
|---|---|---|
| PATENT NO. | : 8,323,258 B2 | Page 1 of 1 |
| APPLICATION NO. | : 11/881515 | |
| DATED | : December 4, 2012 | |
| INVENTOR(S) | : Dalal et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 585 days.

Signed and Sealed this
Second Day of December, 2014

Michelle K. Lee
*Deputy Director of the United States Patent and Trademark Office*